(12) United States Patent
Eisenbach-Schwartz et al.

(10) Patent No.: US 8,828,404 B2
(45) Date of Patent: Sep. 9, 2014

(54) VACCINE AND METHOD FOR TREATMENT OF NEURODEGENERATIVE DISEASES

(75) Inventors: Michal Eisenbach-Schwartz, Rehovot (IL); Ester Yoles, Moshav Beit Gamliel (IL); Oleg Butovsky, Beer Sheva (IL); Jonathan Kipnis, Modiin (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 281 days.

(21) Appl. No.: 13/097,427

(22) Filed: Apr. 29, 2011

(65) Prior Publication Data

US 2011/0206706 A1 Aug. 25, 2011

Related U.S. Application Data

(63) Continuation of application No. 10/578,899, filed as application No. PCT/IL2004/001037 on Nov. 11, 2004, now abandoned, said application No. 10/578,899 is a continuation-in-part of application No. 09/765,644, filed on Jan. 22, 2001, now Pat. No. 6,844,314, which is a continuation-in-part of application No. 09/620,216, filed on Jul. 20, 2000, now abandoned, which is a continuation-in-part of application No. 09/487,793, filed on Jan. 20, 2000, now abandoned.

(60) Provisional application No. 60/518,627, filed on Nov. 12, 2003, provisional application No. 60/610,966, filed on Sep. 20, 2004.

(51) Int. Cl.
*A61K 39/00* (2006.01)
*A61K 38/00* (2006.01)
*A61P 25/28* (2006.01)

(52) U.S. Cl.
CPC ............ *A61K 39/0008* (2013.01); *A61K 39/00* (2013.01); *A61K 2039/5158* (2013.01); *A61K 39/0007* (2013.01)
USPC .... 424/185.1; 514/17.7; 514/17.8; 424/184.1

(58) Field of Classification Search
CPC A61K 2300/00; A61K 38/00; A61K 39/0007
USPC .................. 424/185.1, 184.1; 514/17.7, 17.8
See application file for complete search history.

(56) References Cited

U.S. PATENT DOCUMENTS

| | | | |
|---|---|---|---|
| 6,071,970 A | 6/2000 | Mueller et al. |
| 6,794,414 B1 | 9/2004 | Steinman |
| 7,217,687 B2 | 5/2007 | Boschert et al. |
| 7,220,729 B2 | 5/2007 | Chern |
| 7,718,699 B1 | 5/2010 | Broyles et al. |
| 2002/0037848 A1 | 3/2002 | Eisenbach-Schwartz et al. |

FOREIGN PATENT DOCUMENTS

| | | |
|---|---|---|
| WO | 01/52878 A2 | 7/2001 |
| WO | 01/93893 A2 | 12/2001 |
| WO | 01/97785 A2 | 12/2001 |

OTHER PUBLICATIONS

Carter et al., Characterization of Progressive Motor Deficits in Mice Transgenic for the Human Huntington's Disease Mutation, the Journal of Neuroscience, 19(8):3248-3257 (1999).
Bates et al. "Experimental therapeutics in Huntington's disease: are models useful for therapeutic trials?" Curr Opin Neurol 16:465-470 (2003).
Björkqvist et al. The T6/2 transgenic mouse model of huntington's disease develops diabetes due to deficient b-cell mass and exocytosis, Human Molecular Genetics 14(5): 565-574 (2005).
Huntington's Disease: Hope Through Research (http://www.ninds.nih.gov/disorders/huntington/detail_huntington. htm?css=print.) Internet p. 1-14 (downloaded Jan. 11, 2010).
Schwartz et al., "A common vaccine for fighting neurodegenerative disorders: recharging immunity for homeostasis", Trends in Pharmacological Sciences vol. 25 No. 8, Aug. 2004, pp. 407-412.
Schwartz, "Harnessing the Immune System for Neuroprotection: Therapeutic Vaccines for Acute and Chronic Neurodegenerative Disorders" Cellular and Molecular Neurobiology, vol. 21, No. 6, pp. 617-627 (2001).
Schwartz et al., "Prospects for Therapeutic Vaccination With Glatiramer Acetate for Neurodegenerative Diseases Such as Alzheimer's Disease" Drug Development Research vol. 56 No. 2 pp. 143-149 (2002).
Kipnis et al., "Dual action glatiramer acetate (Cop-1) in the treatment of CNS autoimmune and neurodegenerative disorders" Trends in Molecular vol. 8, No. 7, pp. 319-323 (2002).
Peng et al. "The antidepressant sertraline improves the phenotype, promotes neurogenesis and increases BDNF levels in the R6/2 Huntington's disease mouse model" Exp Neurol. 210(1):154-63 (2008).
What is HD? downloaded Jun. 22, 2010 from (http://www.hdsa.org/about/our-mission/what-is-hd.html) Huntington's disease society of america. p. 1-5. (2010).
Angelov at el, "Therapeutic Vaccine for Acute and Chronic Motor Neuron Diseases: Implications for Amyotrophic Lateral Sclerosis", PNAS, No. 8, vol. 100, pp. 4790-4795 (2003).

*Primary Examiner* — Taeyoon Kim
(74) *Attorney, Agent, or Firm* — Browdy and Neimark, PLLC

(57) ABSTRACT

Methods and compositions are provided for treatment of neurodegenerative diseases in which there is accumulation of misfolded and/or aggregated proteins, excluding prion diseases. In particular, the invention relates to treatment of the neurodegenerative diseases Huntington's disease (HD), Alzheimer's disease (AD) or Parkinson's disease (PD), by administration of an agent selected from the group consisting of (i) Copolymer 1, (ii) a Copolymer 1-related peptide, (iii) a Copolymer 1-related polypeptide, and (iv) T cells activated with (i), (ii) or (iii).

17 Claims, 14 Drawing Sheets

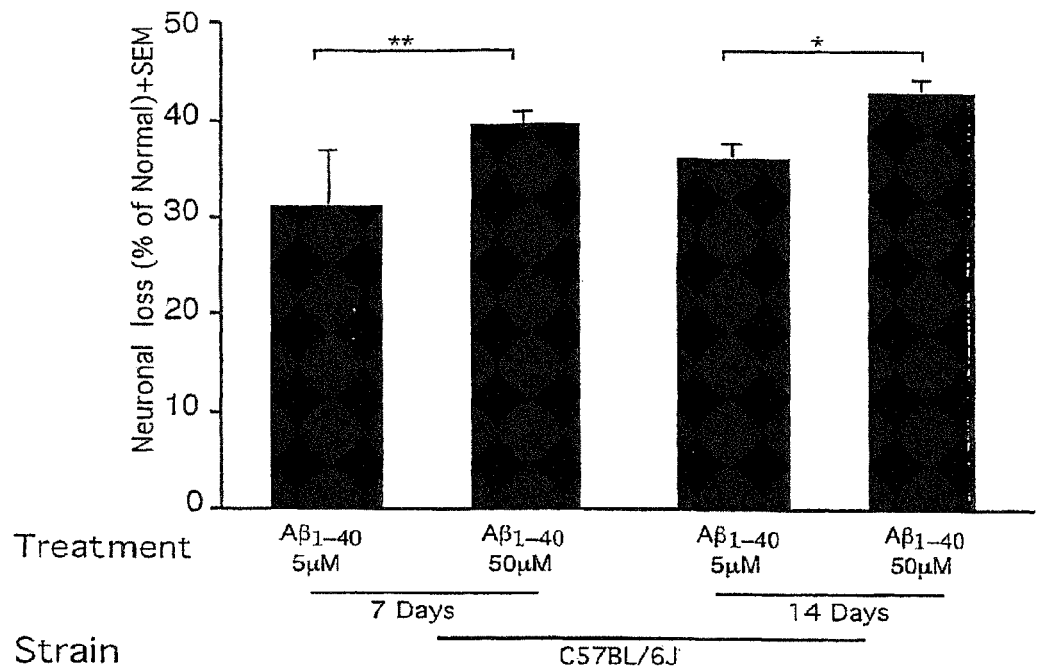
Fig. 11A
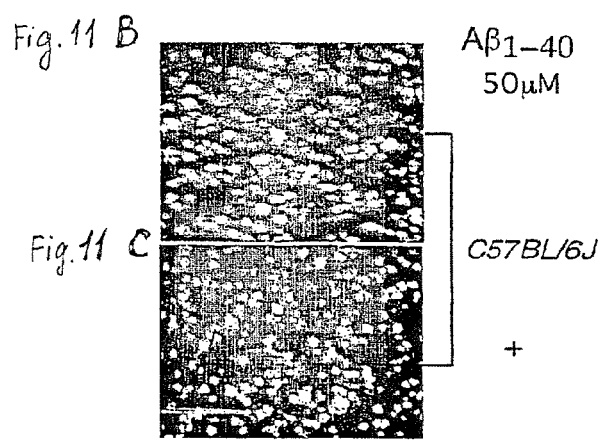

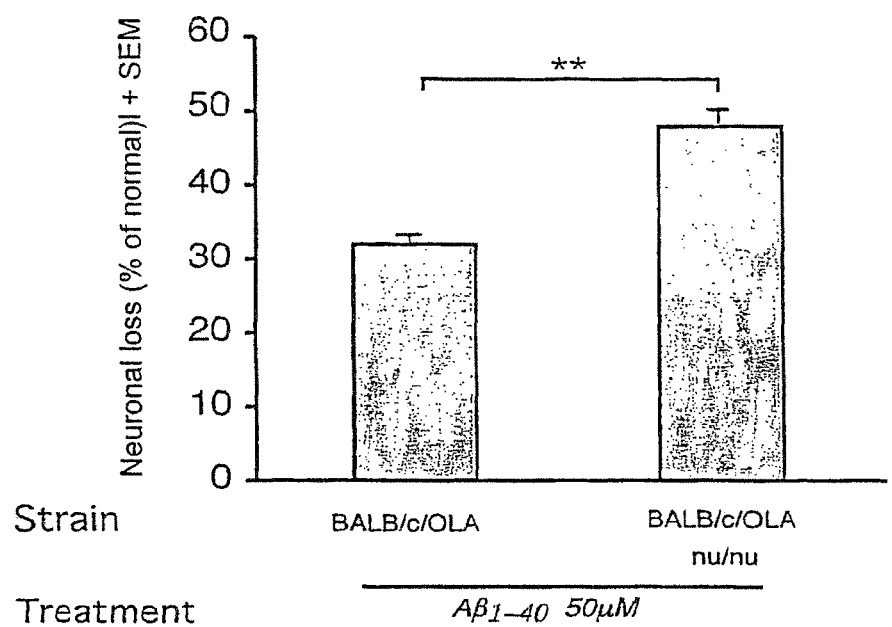
Fig. 11D
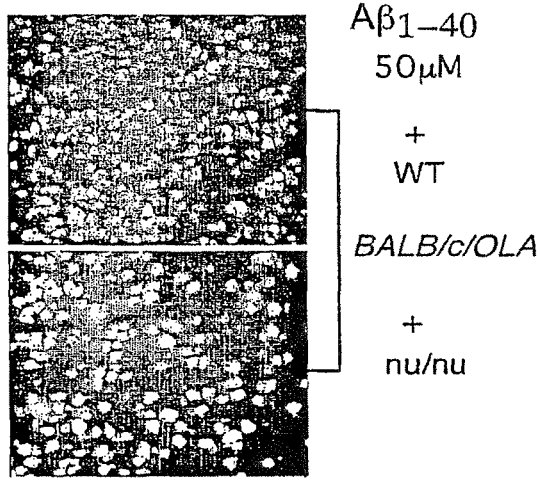
Fig. 11 E
Fig. 11 F

VACCINE AND METHOD FOR TREATMENT OF NEURODEGENERATIVE DISEASES

FIELD OF THE INVENTION

The present invention relates to compositions, e.g. vaccines, and methods for the treatment of neurodegenerative diseases in which there is accumulation of misfolded and/or aggregated proteins, excluding prion diseases. In particular, the invention relates to treatment of the neurodegenerative diseases Huntington's disease (HD), Alzheimer's disease (AD) or Parkinson's disease (PD), by administration of an agent selected from the group consisting of Copolymer 1, a Copolymer 1-related peptide or polypeptide, and T cells activated therewith.

ABBREVIATIONS $A\beta_{1-40}$, β-amyloid peptide 1-40; AD, Alzheimer's disease; APC, antigen-presenting cell; CNS, central nervous system; Cop-1, Copolymer 1; DAT, dopamine transporter; HD, Huntington's disease; IRPB, interphotoreceptor retinoid-binding protein; MPTP, 1-methyl-4-phenyl-1,2,3,6-tetrahydropyridine; OHSC, organotypic hippocampal slice culture; PD, Parkinson's disease; PI, propidium iodide; RGC, retinal ganglion cell; Treg, $CD4^+CD25^+$ regulatory T cells; TUNEL, terminal deoxynucleotidyl transferase biotin-dUTP nick end labeling; WRH, whole retinal homogenate.

BACKGROUND OF THE INVENTION

Pathological Disorders of the CNS Involving Accumulation of Misfolded and/or Aggregated Proteins For many decades, clinicians have been aware of the formation of insoluble protein aggregates in particular diseases. In Alzheimer disease (Selkoe, 1997, 2002), the presence in the CNS of β-amyloid-containing plaques is associated with neurodegeneration and dementia. Similarly, other neurodegenerative diseases have recently been discovered to involve protein aggregation in the brain. For example, prion diseases such as kuru, Creutzfeldt-Jacob disease and bovine spongiform encephalopathy are associated with amyloid deposits of the prion protein (PrP). Polyglutamine repeat diseases such as Huntington disease are likewise associated with neuronal cytosolic and intranuclear inclusions (DiFiglia et al., 1997). These inclusions are composed of fibrils that stain similarly to amyloid (Scherzinger et al., 1997). Finally, in Parkinson disease, inclusions known as Lewy bodies, found in the cytoplasm of cells of the basal ganglia, include amyloid-like aggregates of the protein α-synuclein (Conway et al., 2000; Serpell et al., 2000).

Huntington's disease (HD), identified in the late 1800s by the physician George Huntington, is an autosomal dominant neurodegenerative disease whose symptoms are caused by the loss of cells in the basal ganglia of the brain. This damage to cells affects cognitive ability (thinking, judgment, memory), movement, and emotional control. HD is characterized by uncontrollable, dancelike movements and personality changes. HD patients develop slurred speech, an unsteady walk and difficulty in swallowing. There is no effective treatment for HD. After a long illness, individuals with HD die from complications such as choking or infection.

In 1993, the mutation that causes HD was identified as an unstable expansion of CAG repeats in the IT15 gene encoding huntingtin, a protein of unknown function (Menalled and Chesselet, 2002). The CAG repeat expansion results in an increased stretch of glutamines in the N-terminal portion of the protein, which is widely expressed in brain and peripheral tissues (Gutekunst et al., 1995). The exact mechanisms underlying neuronal death in Huntington's disease remain unknown. Proposed mechanisms have included activation of caspases or other triggers of apoptosis, mitochondrial or metabolic toxicity, and interference with gene transcription. Recent advances in the understanding of the pathophysiology of neurodegenerative diseases in general and of Huntington's disease in particular, have suggested new therapeutic strategies aimed at slowing progression or delay onset of the neurodegenerative disease.

Alzheimer's disease (AD) is an irreversible, progressive brain disorder that occurs gradually and results in memory loss, behavioral and personality changes, and a decline in mental abilities. These losses are related to the death of brain cells and the breakdown of the connections between them. The course of this disease varies from person to person, as does the rate of decline. On average, AD patients live for 8 to 10 years after they are diagnosed, though the disease can last up to 20 years.

AD advances by stages, from early, mild forgetfulness to a severe loss of mental function. At first, AD destroys neurons in parts of the brain that control memory, especially in the hippocampus and related structures. As nerve cells in the hippocampus stop functioning properly, short-term memory fails. AD also attacks the cerebral cortex, particularly the areas responsible for language and reasoning Eventually, many other areas of the brain are involved.

Parkinson's disease (PD) is an idiopathic, slowly progressive, degenerative CNS disorder characterized by slow and decreased movement, muscular rigidity, resting tremor, and postural instability. Despite extensive investigations, the cause of PD remains unknown. The loss of substantia nigra neurons, which project to the caudate nucleus and putamen, results in the depletion of the neurotransmitter dopamine in these areas. Significant hints into PD pathogenesis have been yielded by the use of 1-methyl-4-phenyl-1,2,4,6-tetrandropyridine (MPTP), a neurotoxin that replicates most of the neuropathological hallmarks of PD in humans, nonhuman primates, and other mammalian species, including mice. Although the MPTP mouse model departs from human PD in a few important ways, it offers a unique means to investigate, in vivo, molecular events underlying the demise of midbrain dopaminergic neurons (Dauer and Przedborski, 2003).

Acute and/or chronic neuronal loss in the adult CNS results in the irreversible loss of function due to the very poor ability of mature nerve cells to proliferate and compensate for the lost neurons. Thus attenuating or reducing neuronal loss is essential for preservation of function. In most of the neurodegenerative diseases like Alzheimer's disease, Parkinson's disease, amyotrophic lateral sclerosis (ALS) and Huntington's disease, the etiology is not clear, hence they are incurable. Nevertheless, there are some primary and secondary risk factors, which are the target for therapeutic intervention aiming at inhibiting or attenuating progress of neuronal loss, collectively termed as neuroprotective therapy. Some of the risk factors are disease-specific but others, like excitatory amino acids, free radicals and nitric oxide, are common to all the neurodegenerative disorders. These factors are essential self-components in the healthy CNS, but with their accumulation in excess amounts in the degenerative tissue, they become cytotoxic leading to the spread of damage beyond the initial cause of neuron death.

Glutamate is one of the most common mediators of toxicity in acute and chronic degenerative disorders like status epilepticus, cerebral ischemia, traumatic brain injury, ALS, Huntington's disease, lathyrisms and Alzheimer's disease.

Glutamate is a primary excitatory neurotransmitter in the human CNS. L-glutamate is present at a majority of synapses and is capable of displaying dual activity: it plays a pivotal role in normal functioning as an essential neurotransmitter, but becomes toxic when its physiological levels are exceeded.

In order to minimize neuronal loss (neuroprotection) several approaches have been adopted, at which the most common is targeting the risk factors in an attempt to neutralize or inhibit their action. Unfortunately, these therapeutic strategies showed marginal efficacy in human subjects with concomitant severe side effects. The failure of agents with discrete singular mechanisms of action argues for a multi-pronged approach.

Protective Autoimmunity

Loss of neurons in patients with devastating chronic neurodegenerative disorders is attributed to numerous factors, most of them (for example, oxidative stress, ion imbalance, metabolic deficits, neurotransmitter imbalance, neurotoxicity) common to all such diseases (Doble, 1999). Even those factors that are apparently unique to a particular disorder share certain common features, including changes in the extracellular deposition of self-compounds resulting in conformational and other changes, as well as in their aggregation, often culminating in plaque formation (Hardy and Selkoe, 2002).

The local immune response to injuries in the CNS has often been blamed for the progressive neurodegeneration that occurs after an insult (Hauben and Schwartz, 2003). Studies in the inventors' laboratory, however, have challenged the long-held notion that activated microglia or blood-borne activated macrophages contribute to the ongoing pathology, and suggest instead that these immune cells are harnessed to aid recovery, but may be unable to display a significant positive effect because they fail to acquire the necessary phenotype (activity) or because their intervention is not strong enough or is inappropriately timed. This suggestion was supported by the demonstration that, in rats, macrophages activated by peripheral nerve (Rapalino et al., 1998) or by skin (Bomstein et al., 2003) can be helpful in promoting recovery from spinal cord injury. The functional activity of such macrophages was recently found to resemble that of APC (Bomstein et al., 2003).

Subsequent studies by the inventors suggested that after a mechanical or biochemical insult to the CNS the local immune response, which is mediated by T cells directed against self-antigens residing in the site of the lesion (i.e., autoimmune T cells), determines the ability of the neural tissue to withstand the unfriendly extracellular conditions resulting from the injury. It thus seems that the body protects itself against toxic self-compounds in the CNS by harnessing a peripheral adaptive immune response in the form of T cells specific to antigens residing in the site of damage (Hauben et al., 2000a; Moalem et al., 1999a; Yoles et al., 2001; Schori et al., 2001a; Schori et al., 2001b). The T cells that mediate protection are directed not against a particular threatening self-compound but rather against dominant self-antigens that reside at the lesion site (Mizrahi et al., 2002; Schwartz et al., 2003; Bakalash et al., 2002).

Further studies by the inventors suggested that T-cell specificity is needed in order to ensure that among the T cells that arrive at the site, those encountering their specific or cross-reactive antigens (presented to them by local microglia acting as APC) will become activated. The activated T cells can then provide the necessary cytokines or growth factors that control the activity of the local microglia and the friendliness of the extracellular milieu (Schwartz et al., 2003; Moalem et al., 2000; Kipnis et al., 2000).

The concept of T cell-dependent "protective autoimmunity" has been formulated by the inventor Prof. Michal Schwartz and her group (Kipnis et al., 2002a; Schwartz and Kipnis, 2002a). According to this concept, an acute or chronic insult to the CNS triggers an autoimmune response directed against proteins residing in the lesion site. T cells homing to the lesion site are activated by cells presenting the relevant antigen. Once activated, they augment and control local immune cells, allowing efficient removal of toxic compounds and tissue debris, thus protecting the damaged nerves from further degeneration. The potential of the immune system to counteract the hostile conditions is enhanced by boosting the normal immune response. Based on this hypothesis, boosting the immune system with a suitable antigen should provide neuroprotection. Among suitable antigens identified by the present inventors is Copolymer 1.

Copolymer 1

Copolymer 1, also called Cop 1, is a random non-pathogenic synthetic copolymer, a heterogeneous mix of polypeptides containing the four amino acids L-glutamic acid (E), L-alanine (A), L-tyrosine (Y) and L-lysine (K) in an approximate ratio of 1.5:4.8:1:3.6, but with no uniform sequence. Although its mode of action remains controversial, Cop 1 clearly helps retard the progression of human multiple sclerosis (MS) and of the related autoimmune condition studied in mice, experimental autoimmune encephalomyelitis (EAE). One form of Cop 1, known as glatiramer acetate, has been approved in several countries for the treatment of multiple sclerosis under the trademark Copaxone® (Teva Pharmaceutical Industries Ltd., Petach Tikva, Israel).

Vaccination with Cop 1 or with Cop 1-activated T cells have been shown by the present inventors to boost the protective autoimmunity, after traumatic CNS insult, thereby reducing further injury-induced damage, and can further protect CNS cells from glutamate toxicity. Reference is made to Applicant's previous U.S. patent application Ser. Nos. 09/765,301 and 09/765,644 and corresponding published International Application Nos. WO 01/52878 and WO 01/93893, which disclose that Cop 1, Cop 1-related peptides and polypeptides and T cells activated therewith prevent or inhibit neuronal degeneration and promote nerve regeneration in the CNS or peripheral nervous system (PNS), and protect CNS cells from glutamate toxicity.

Prof. Schwartz and colleagues have shown that Cop 1 acts as a low-affinity antigen that activates a wide range of self-reacting T cells, resulting in neuroprotective autoimmunity that is effective against both CNS white matter and grey matter degeneration (Kipnis et al., 2002a; Schwartz and Kipnis, 2002a). The neuroprotective effect of Cop 1 vaccination was demonstrated by the inventors in animal models of acute and chronic neurological disorders such as optic nerve injury (Kipnis et al., 2000), head trauma (Kipnis et al., 2003), glaucoma (Schori et al., 2001b), amyotrophic lateral sclerosis (Angelov et al., 2003) and in the applicant's patent applications WO 01/52878, WO 01/93893 and WO 03/047500.

The use of Copolymer 1 for treatment of prion-related diseases is disclosed in WO 01/97785. Gendelman and co-workers disclose that passive immunization with splenocytes of mice immunized with Cop 1 confers dopaminergic neuroprotection in MPTP-treated mice (Benner et al., 2004).

All patents and patent applications cited herein are hereby incorporated by reference in their entirety as if fully disclosed herein.

SUMMARY OF THE INVENTION

The present invention relates, in one aspect, to a method for treating a neurodegenerative disorder or disease in which there is accumulation of misfolded and/or aggregated proteins, excluding prion-related diseases, said method comprising administering to an individual in need an agent selected from the group consisting of (i) Copolymer 1, (ii) a Copolymer 1-related peptide, (iii) a Copolymer 1-related polypeptide, and (iv) T cells activated with (i), (ii) or (iii).

In one embodiment, the invention relates to a method for reducing disease progression, and/or protection from neurodegeneration and/or protection from glutamate toxicity in a patient suffering from a neurodegenerative disorder or disease in which there is accumulation of misfolded and/or aggregated proteins, excluding prion-related diseases, which comprises administering to said patient a therapeutically active amount of an agent selected from the group consisting of (i) Copolymer 1, (ii) a Copolymer 1-related peptide, (iii) a Copolymer 1-related polypeptide, and (iv) T cells activated with (i), (ii) or (iii).

In another embodiment, the invention relates to a method for reducing disease progression, and/or protection from neurodegeneration and/or protection from glutamate toxicity in a patient suffering from a neurodegenerative disorder or disease in which there is accumulation of misfolded and/or aggregated proteins, excluding prion-related diseases, which comprises immunizing said patient with an agent selected from the group consisting of (i) Copolymer 1, (ii) a Copolymer 1-related peptide, (iii) a Copolymer 1-related polypeptide, and (iv) T cells activated with (i), (ii) or (iii).

In another aspect, the present invention provides a pharmaceutical composition for treatment of a neurodegenerative disorder or disease in which there is accumulation of misfolded and/or aggregated proteins, excluding prion-related diseases, comprising a pharmaceutically acceptable carrier and an active agent selected from the group consisting of (i) Copolymer 1, (ii) a Copolymer 1-related peptide, (iii) a Copolymer 1-related polypeptide, and (iv) T cells activated with (i), (ii) or (iii). In one embodiment, said pharmaceutical composition is a vaccine.

In a further aspect, the present invention relates to the use of an active agent selected from the group consisting of (i) Copolymer 1, (ii) a Copolymer 1-related peptide, (iii) a Copolymer 1-related polypeptide, and (iv) T cells activated with (i), (ii) or (iii), for the manufacture of a pharmaceutical composition for treatment of a neurodegenerative disorder or disease in which there is accumulation of misfolded and/or aggregated proteins, excluding prion-related diseases. In one embodiment, said pharmaceutical composition is a vaccine.

In one embodiment, said neurodegenerative disease or disorder is Huntington's disease. In another embodiment, said neurodegenerative disease or disorder is Alzheimer's disease. In a further embodiment, said neurodegenerative disease or disorder is Parkinson's disease.

In still another aspect, the invention provides an article of manufacture comprising packaging material and a pharmaceutical composition contained within the packaging material, said pharmaceutical composition comprising an agent selected from the group consisting of Copolymer 1, a Copolymer 1-related peptide, and a Copolymer 1-related polypeptide; and said packaging material includes a label that indicates that said agent is therapeutically effective for treating a neurodegenerative disease or disorder selected from Huntington's disease, Alzheimer's disease or Parkinson's disease.

In the most preferred embodiment of the invention, the active agent is Copolymer 1.

BRIEF DESCRIPTION OF THE FIGURES

FIGS. 11A-11F show that susceptibility of retinal ganglion cells to $A\beta_{1-40}$ toxicity is T cell-dependent. (A) C57BL/6/J mice were injected intravitreally with 5 or 50 µM $A\beta_{1-40}$ or were not injected (control), and 1 or 2 weeks later the retinas were excised and the surviving RGCs counted. Relative to controls, significantly more neurons were lost in mice that had received the higher dose of $A\beta_{1-40}$ ($P<0.001$ and $P<0.0001$ at 1 and 2 weeks, respectively, two-tailed Student's t-test). Values shown are from one of three independent experiments with similar results (n=6-8 mice per group). Injection of the vehicle resulted in a small loss of RGCs relative to controls. (B) and (C), representative micrographs of retinas injected or not injected with $A\beta_{1-40}$. (D) BALB/c/OLA mice [wild type or nu/nu (devoid of mature T cells)] were injected intravitreally with $A\beta_{1-40}$ (50 µM). Significantly more RGCs were lost in the nu/nu mice relative to the wild-type ($P<0.001$, two-tailed Student's t-test) Values shown are from one of three independent experiments with similar results (n=5-7 mice per group). (E) and (F), representative micrographs of retinas from wild-type BALB/c/OLA and nu/nu BALB/c/OLA mice injected with $A\beta_{1-40}$.

DETAILED DESCRIPTION OF THE INVENTION

Figure 1:
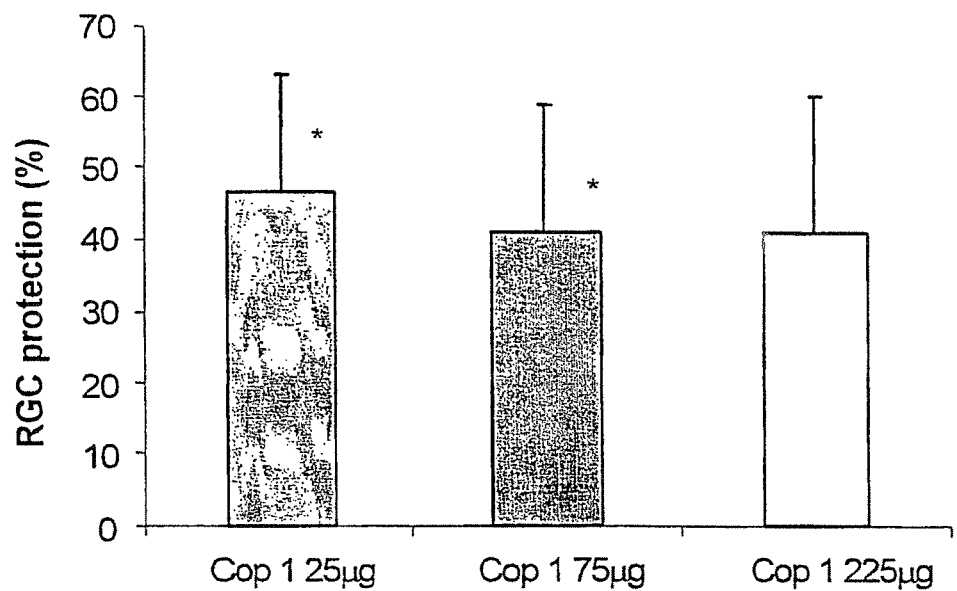
FIG. 1 shows the neuroprotective effect on retinal ganglion cells (RGCs) of mice by immunization with different doses of Cop 1 (25, 75 g or 225 µg/mouse) injected 7 days before exposure of RGCs to glutamate toxicity. The results are presented as mean±SEM of percentage of RGCs that were protected due to Cop 1 vaccination out of the total RGC death in the non-treated group. * represents statistically significant difference (t-test, p<0.05) versus the non-treated group.

The methods of the present invention comprise administering to an individual in need an agent selected from the group consisting of (i) Copolymer 1, (ii) a Copolymer 1-related peptide, (iii) a Copolymer 1-related polypeptide, and (iv) T cells activated with (i), (ii) or (iii), for the treatment of a neurodegenerative disorder or disease in which there is accumulation of misfolded and/or aggregated proteins, excluding prion-related diseases. In one preferred embodiment, the neurodegenerative disease or disorder is Huntington's disease. In another preferred embodiment, the neurodegenerative disease or disorder is Alzheimer's disease. In a further preferred embodiment, the neurodegenerative disease or disorder is Parkinson's disease.

The treatment with Copolymer 1, Cop 1-related peptides or polypeptides, of T cells activated therewith, aims to reduce disease progression, to afford protection from neurodegeneration, and/or to afford protection from glutamate toxicity in patients suffering from Huntington's disease, Alzheimer's disease or Parkinson's disease. In one embodiment, the treatment is performed by immunization. In another embodiment, therapeutically effective amounts of the selected agent are administered to the patient. The doses and regimen of the two types of treatment may be different.

Further provided by the present invention is a method for treating or preventing neurodegeneration and cognitive decline and dysfunction associated with Huntington's disease, Alzheimer's disease or Parkinson's disease, said method comprising administering to an individual in need an agent selected from the group consisting of (i) Copolymer 1, (ii) a Copolymer 1-related peptide, (iii) a Copolymer 1-related polypeptide, and (iv) T cells activated with (i), (ii) or (iii).

As used herein in the application, the terms "Cop 1" and "Copolymer 1" are used interchangeably.

For the purpose of the present invention, "Cop 1 or a Cop 1-related peptide or polypeptide" is intended to include any peptide or polypeptide, including a random copolymer, that cross-reacts functionally with myelin basic protein (MBP) and is able to compete with MBP on the MHC class II in the antigen presentation.

The composition or vaccine of the invention may comprise as active agent a Cop 1 or a Cop 1-related peptide or polypeptide represented by a random copolymer consisting of a suitable ratio of a positively charged amino acid such as lysine or arginine, in combination with a negatively charged amino acid (preferably in a lesser quantity) such as glutamic acid or aspartic acid, optionally in combination with a non-charged neutral amino acid such as alanine or glycine, serving as a filler, and optionally with an amino acid adapted to confer on the copolymer immunogenic properties, such as an aromatic amino acid like tyrosine or tryptophan. Such compositions may include any of those copolymers disclosed in WO 00/05250, the entire contents of which are herewith incorporated herein by reference.

More specifically, the composition for use in the present invention comprises at least one copolymer selected from the group consisting of random copolymers comprising one amino acid selected from each of at least three of the following groups: (a) lysine and arginine; (b) glutamic acid and aspartic acid; (c) alanine and glycine; and (d) tyrosine and tryptophan.

The copolymers for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make the copolymers used in the present invention. The present invention contemplates the use of copolymers containing both D- and L-amino acids, as well as copolymers consisting essentially of either L- or D-amino acids.

In one embodiment of the invention, the copolymer contains four different amino acids, each from a different one of the groups (a) to (d).

In a more preferred embodiment, the pharmaceutical composition or vaccine of the invention comprises Copolymer 1, a mixture of random polypeptides consisting essentially of the amino acids L-glutamic acid (E), L-alanine (A), L-tyrosine (Y) and L-lysine (K) in an approximate ratio of 1.5:4.8:1:3.6, having a net overall positive electrical charge and of a molecular weight from about 2 KDa to about 40 KDa. In one preferred embodiment, the Cop 1 has average molecular weight of about 2 KDa to about 20 KDa, more preferably of about 4.7 KDa to about 13 KDa, still more preferably of about 4 KDa to about 8.6 KDa, of about 5 KDa to 9 KDa, or of about 6.25 KDa to 8.4 KDa. In another preferred embodiment, the Cop 1 has average molecular weight of about 13 KDa to about 20 KDa, more preferably of about 13 KDa to about 16 KDa or of about 15 KDa to about 16 KDa. Other average molecular weights for Cop 1, lower than 40 KDa, are also encompassed by the present invention. Copolymer 1 of said molecular weight ranges can be prepared by methods known in the art, for example by the processes described in U.S. Pat. No. 5,800,808, the entire contents of which are hereby incorporated by reference in the entirety. The Copolymer 1 may be a polypeptide comprising from about 15 to about 100, preferably from about 40 to about 80, amino acids in length. In one preferred embodiment, the Cop 1 is in the form of its acetate salt known under the generic name glatiramer acetate, that has been approved in several countries for the treatment of multiple sclerosis (MS) under the trade name, Copaxone® (a trademark of Teva Pharmaceuticals Ltd., Petach Tikva, Israel). The activity of Copolymer 1 for the vaccine disclosed herein is expected to remain if one or more of the following substitutions is made: aspartic acid for glutamic acid, glycine for alanine, arginine for lysine, and tryptophan for tyrosine.

In another embodiment of the invention, the Cop 1-related peptide or polypeptide is a copolymer of three different amino acids each from a different one of three groups of the groups (a) to (d). These copolymers are herein referred to as terpolymers.

In one embodiment, the Cop 1-related peptide or polypeptide is a terpolymer containing tyrosine, alanine, and lysine, hereinafter designated YAK, in which the average molar fraction of the amino acids can vary: tyrosine can be present in a mole fraction of about 0.05-0.250; alanine in a mole fraction of about 0.3-0.6; and lysine in a mole fraction of about 0.1-0.5. More preferably, the molar ratios of tyrosine, alanine and lysine are about 0.10:0.54:0.35, respectively. It is possible to substitute arginine for lysine, glycine for alanine, and/or tryptophan for tyrosine.

In another embodiment, the Cop 1-related peptide or polypeptide is a terpolymer containing tyrosine, glutamic acid, and lysine, hereinafter designated YEK, in which the average molar fraction of the amino acids can vary: glutamic acid can be present in a mole fraction of about 0.005-0.300, tyrosine can be present in a mole fraction of about 0.005-0.250, and lysine can be present in a mole fraction of about 0.3-0.7. More preferably, the molar ratios of glutamic acid, tyrosine, and lysine are about 0.26:0.16:0.58, respectively. It is possible to substitute aspartic acid for glutamic acid, arginine for lysine, and/or tryptophan for tyrosine.

In another preferred embodiment, the Cop 1-related peptide or polypeptide is a terpolymer containing lysine, glutamic acid, and alanine, hereinafter designated KEA, in which the average molar fraction of the amino acids can vary: glutamic acid can be present in a mole fraction of about 0.005-0.300, alanine in a mole fraction of about 0.005-0.600, and lysine can be present in a mole fraction of about 0.2-0.7. More preferably, the molar ratios of glutamic acid, alanine and lysine are about 0.15:0.48:0.36, respectively. It is possible to substitute aspartic acid for glutamic acid, glycine for alanine, and/or arginine for lysine.

In a preferred embodiment, the Cop 1-related peptide or polypeptide is a terpolymer containing tyrosine, glutamic acid, and alanine, hereinafter designated YEA, in which the average molar fraction of the amino acids can vary: tyrosine can be present in a mole fraction of about 0.005-0.250, glutamic acid in a mole fraction of about 0.005-0.300, and alanine in a mole fraction of about 0.005-0.800. More preferably, the molar ratios of glutamic acid, alanine, and tyrosine are about 0.21:0.65:0.14, respectively. It is possible to substitute tryptophan for tyrosine, aspartic acid for glutamic acid, and/or glycine for alanine.

The average molecular weight of the terpolymers YAK, YEK, KEA and YEA can vary between about 2 KDa to 40 KDa, preferably between about 3 KDa to 35 KDa, more preferably between about 5 KDa to 25 KDa.

Copolymer 1 and related peptides and polypeptides may be prepared by methods known in the art, for example, under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example dicyclohexylcarbodiimide, can be used to facilitate the formation of the peptide bond. Blocking groups can be used to protect functional groups, such as the side chain moieties and some of the amino or carboxyl groups against undesired side reactions.

For example, the copolymers can be prepared by the process disclosed in U.S. Pat. No. 3,849,550, wherein the N-carboxyanhydrides of tyrosine, alanine, γ-benzyl glutamate and N ε-trifluoroacetyl-lysine are polymerized at ambient temperatures (20° C.-26° C.) in anhydrous dioxane with diethylamine as an initiator. The γ-carboxyl group of the glutamic acid can be deblocked by hydrogen bromide in glacial acetic acid. The trifluoroacetyl groups are removed from lysine by 1 M piperidine. One of skill in the art readily understands that the process can be adjusted to make peptides and polypeptides containing the desired amino acids, that is, three of the four amino acids in Copolymer 1, by selectively eliminating the reactions that relate to any one of glutamic acid, alanine, tyrosine, or lysine.

The molecular weight of the copolymers can be adjusted during polypeptide synthesis or after the copolymers have been made. To adjust the molecular weight during polypeptide synthesis, the synthetic conditions or the amounts of amino acids are adjusted so that synthesis stops when the polypeptide reaches the approximate length which is desired. After synthesis, polypeptides with the desired molecular weight can be obtained by any available size selection procedure, such as chromatography of the polypeptides on a molecular weight sizing column or gel, and collection of the molecular weight ranges desired. The copolymers can also be partially hydrolyzed to remove high molecular weight species, for example, by acid or enzymatic hydrolysis, and then purified to remove the acid or enzymes.

In one embodiment, the copolymers with a desired molecular weight may be prepared by a process, which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process, which includes reacting the protected polypeptide with hydrobromic acid for a time and at a temperature predetermined by test reaction. The trifluoroacetyl-polypeptide with the desired molecular weight profile is then further treated with an aqueous piperidine solution to form a low toxicity polypeptide having the desired molecular weight.

In a preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

As binding motifs of Cop 1 to MS-associated HLA-DR molecules are known (Fridkis-Hareli et al, 1999), polypeptides derived from Cop 1 having a defined sequence can readily be prepared and tested for binding to the peptide binding groove of the HLA-DR molecules as described in the Fridkis-Hareli et al (1999) publication. Examples of such peptides are those disclosed in WO 00/05249 and WO 00/05250, the entire contents of which are hereby incorporated herein by reference, and include the peptides of SEQ ID NOs. 1-32 hereinbelow.

| SEQ ID NO. | Peptide Sequence |
|---|---|
| 1 | AAAYAAAAAKAAAA |
| 2 | AEKYAAAAAAKAAAA |
| 3 | AKEYAAAAAAKAAAA |
| 4 | AKKYAAAAAAKAAAA |
| 5 | AEAYAAAAAAKAAAA |
| 6 | KEAYAAAAAAKAAAA |
| 7 | AEEYAAAAAAKAAAA |
| 8 | AAEYAAAAAAKAAAA |
| 9 | EKAYAAAAAAKAAAA |
| 10 | AAKYEAAAAAKAAAA |
| 11 | AAKYAEAAAAKAAAA |
| 12 | EAAYAAAAAAKAAAA |
| 13 | EKKYAAAAAAKAAAA |
| 14 | EAKYAAAAAAKAAAA |
| 15 | AEKYAAAAAAAAAA |
| 16 | AKEYAAAAAAAAAA |
| 17 | AKKYEAAAAAAAAA |
| 18 | AKKYAEAAAAAAAA |

-continued

| SEQ ID NO. | Peptide Sequence |
|---|---|
| 19 | AEAYKAAAAAAAAA |
| 20 | KEAYAAAAAAAAAA |
| 21 | AEEYKAAAAAAAAA |
| 22 | AAEYKAAAAAAAAA |
| 23 | EKAYAAAAAAAAAA |
| 24 | AAKYEAAAAAAAAA |
| 25 | AAKYAEAAAAAAAA |
| 26 | EKKYAAAAAAAAAA |
| 27 | EAKYAAAAAAAAAA |
| 28 | AEYAKAAAAAAAAA |
| 29 | AEKYAAAAAAAAAA |
| 30 | EKYAAAAAAAAAAA |
| 31 | AYKAEAAAAAAAAA |
| 32 | AKYAEAAAAAAAAA |

Such peptides and other similar peptides derived from Cop 1 would be expected to have similar activity as Cop 1. Such peptides, and other similar peptides, are also considered to be within the definition of Cop 1-related peptides or polypeptides and their use is considered to be part of the present invention.

The definition of "Cop 1-related peptide or polypeptide" according to the invention is meant to encompass other synthetic amino acid copolymers such as the random four-amino acid copolymers described by Fridkis-Hareli et al., 2002 (as candidates for treatment of multiple sclerosis), namely copolymers (14-, 35- and 50-mers) containing the amino acids phenylalanine, glutamic acid, alanine and lysine (poly FEAK), or tyrosine, phenylalanine, alanine and lysine (poly YFAK), and any other similar copolymer to be discovered that can be considered a universal antigen similar to Cop 1.

In another embodiment, the present invention relates to the treatment of a neurodegenerative disease or disorder selected from Huntington's disease, Alzheimer's disease or Parkinson's disease, which comprises administering to a patient in need T cells which have been activated preferably in the presence of Cop 1, or by a Cop 1-related peptide or polypeptide. Such T cells are preferably autologous, most preferably of the CD4 and/or CD8 phenotypes, but they may also be allogeneic T cells from related donors, e.g., siblings, parents, children, or HLA-matched or partially matched, semi-allogeneic or fully allogeneic donors. T cells for this purpose are described in U.S. Ser. No. 09/756,301 and U.S. Ser. No. 09/765,644, corresponding to WO 01/93893, each and all of them hereby incorporated by reference in its entirety as if fully disclosed herein.

The dosage of Cop 1 to be administered will be determined by the physician according to the age of the patient and stage of the disease and may be chosen from a range of 1-80 mg, preferably 20 mg, although any other suitable dosage is encompassed by the invention. The treatment should be preferably carried out by administration of repeated doses at suitable time intervals, preferably every 1, 4 or 6 weeks, but any other suitable interval between the immunizations is envisaged by the invention according to the neurodegenerative disease to be treated, the age and condition of the patient.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

For the purposes of the present invention, the composition comprising Copolymer 1 or a Copolymer 1-related peptide or polypeptide is administered in a regimen that confers protective autoimmunity and is sometimes referred to herein as a vaccine for neuroprotective vaccination. Such a vaccine, if desired, may contain Copolymer 1 emulsified in an adjuvant suitable for human clinical use.

Thus, according to the present agent, the active agent may be administered without any adjuvant or it may be emulsified in an adjuvant suitable for human clinical use. The adjuvant is selected from aluminum hydroxide, aluminum hydroxide gel, and aluminum hydroxyphosphate, or any other adjuvant that is found to be suitable for human clinical use. In a preferred embodiment, the vaccine adjuvant is amorphous aluminum hydroxyphosphate having an acidic isoelectric point and an Al:P ratio of 1:1 (herein referred to as Alum-phos). It is clear that this is given by way of example only, and that the vaccine can be varied both with respect to the constituents and relative proportions of the constituents.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

According to the present invention, Cop 1 or a Cop 1-related peptide or polypeptide may be used as a sole therapy or in combination with one or more drugs for the treatment of Alzheimer's, Huntington's or Parkinson's disease. When administered together with another drug or drugs suitable for treatment of Alzheimer's, Huntington's or Parkinson's disease, the additional drug or drugs is/are administered at the same day of vaccination, and daily or at any other interval thereafter, according to the manufacturer's instructions, with no association to the vaccine regimen.

The invention will now be illustrated by the following non-limiting examples.

EXAMPLES

Section I: Vaccination With Cop 1 for Treatment of Huntington'S Disease

Various mouse models for Huntington's disease have been established which enable the exploration of early pathological, molecular and cellular abnormalities produced by the CAG mutation. The HD R6/2 transgenic mice model was selected as the in vivo test system in the present invention. These mice overexpress exon 1 of the human Huntington's disease gene with an increased CAG repeat length that encodes huntingtin (Mangiarini et al., 1996). HD R6/2 transgenic mice show behavioral-motor deficits at as early as 5-6 weeks of age. Behavioral anomalies do not appear until 8 weeks, followed by the development of a progressive severe neurological phenotype with low weight, clasping, tremor and convulsions, and an early death at 10-14 weeks (Carter et al., 1999).

Based on the glutamate toxicity model, an optimal neuroprotective effect in mice was established by a regimen of repeated injections of 75 µg Cop 1 at 4 weeks interval. The same regimen of treatment was found beneficial to HD R6/2 transgenic mice and reduced the rate of motor function deterioration, as shown by a significant preservation of the rotarod performance and prolonged life span of the animals.

Materials and Methods—Section I (i) Animals.

Mice of the C57BL/6J strain, aged 8-13 weeks, were supplied by the Animal Breeding Center of The Weizmann Institute of Science (Rehovot, Israel). Prior to their use in the experiments, the mice were anesthetized by intraperitoneal administration of 80 mg/kg ketamine and 16 mg/kg xylazine. Transgenic R6/2 mice overexpressing the human gene encoding huntingtin were obtained from the Jackson Laboratory. All animals were handled according to the regulations formulated by the Institutional Animal Care and Use Committee (IACUC).

(ii) Reagents.

Copolymer 1 (median MW: 7,200 dalton) was supplied by Teva Pharmaceutical Industries Ltd. (Petach Tikva, Israel).

(iii) Immunization.

For immunization, Cop 1 dissolved in phosphate-buffered saline (PBS; 100 µl) was injected subcutaneously (SC) at one site in the flank of the mice. Control mice were injected with vehicle only.

(iv) Glutamate Injection.

The right eye of an anesthetized C57B BL/6J mouse was punctured with a 27-gauge needle in the upper part of the sclera, and a 10-µl Hamilton syringe with a 30-gauge needle was inserted as far as the vitreal body. Mice were injected intraocularly with a total volume of 1 µl (200 nmol) of L-glutamate dissolved in saline.

(v) Labeling of Retinal Ganglion Cells (RGC) in Mice.

RGCs were labeled 72 hours before the end of the experiment. Mice were anesthetized and placed in a stereotactic device. The skull was exposed and kept dry and clean. The bregma was identified and marked. The designated point of injection was at a depth of 2 mm from the brain surface, 2.92 mm behind the bregma in the anteroposterior axis and 0.5 mm lateral to the midline. A window was drilled in the scalp above the designated coordinates in the right and left hemispheres. The neurotracer dye FluoroGold (5% solution in saline; Fluorochrome, Denver, Colo.) was then applied (1 µl, at a rate of 0.5 µl/min in each hemisphere) using a Hamilton syringe, and the skin over the wound was sutured. Retrograde uptake of the dye provides a marker of the living cells.

(vi) Assessment of RGC Survival in Mice.

Mice were given a lethal dose of pentobarbitone (170 mg/kg). Their eyes were enucleated and the retinas were detached and prepared as flattened whole mounts in paraformaldehyde (4% in PBS). Labeled cells from 4-6 selected fields of identical size (0.5 mm$^2$) were counted. The selected fields were located at approximately the same distance from the optic disk (0.3 mm) to overcome the variation in RGC density as a function of distance from the optic disk. Fields were counted under the fluorescence microscope (magnification× 900) by observers blinded to the treatment received by the mouse. The average number of RGCs per field in each retina was calculated. The effectiveness of the different vaccine formulations in protecting neurons is measured by counting the surviving RGCs.

Example 1

Glutamate Toxicity—an In Vivo Model for Selection of Dose and Regimen of Cop 1 Vaccination Glutamate is an amino acid normally present at low concentrations in the CNS, where it serves as the principal excitatory neurotransmitter. However, in many neurodegenerative diseases, glutamate levels rise to toxic levels, causing cell damage. This model was therefore chosen to establish Cop 1 neuroprotective vaccination and optimize the therapeutic regimen. Glutamate toxicity is assessed by intraocular injection of glutamate into the eyes of C57Bl/6J mice and then measuring the subsequent death of RGCs, the neurons that carry visual signals to the brain.

1a. Cop 1 Dose Determination

To study the effect of the dose of Cop 1 vaccination on glutamate-induced RGC death, Cop 1 emulsified in complete Freund's adjuvant (CFA; 25, 75 or 225 µg Cop 1 in total volume of 100 µl) was injected subcutaneously at one site in the flank of C57BL/6J mice, and seven days later glutamate (200 nmol) was injected into the vitreal body of the mice. After seven days, the surviving RGCs were counted. The amount of RGCs death following glutamate toxicity without any prior immunization was taken as 100% of protectable cells. The results, presented in FIG. 1, show that effective vaccination was obtained by treatment with either 25 µg or 75 µg Cop 1.

Figure 2:
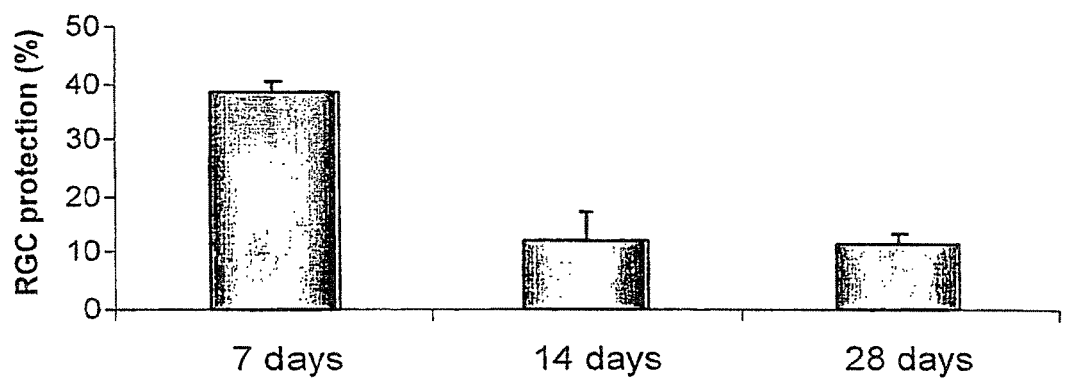
FIG. 2 shows the latency of neuroprotective effect on RGCs of mice by vaccination with 75 µg Cop 1 injected 7, 14 and 28 days before exposure of RGCs to glutamate toxicity.

Latency of neuroprotective effect was determined by vaccination with 75 µg Cop 1 seven, fourteen and twenty-eight days prior to glutamate injection. As can be seen in FIG. 2, the neuroprotective effect of a single injection of Cop 1 is optimal at 7 days post-immunization (reduction of RGC death by ≥40%). The neuroprotective effect was reduced 14 and 28 days after vaccination.

1b. Optimal Regimen of Repeated Cop 1 Injections

In an attempt to maintain the neuroprotective effect of Cop 1 immunization, repeated injections of Cop 1 were evaluated. The aim was to determine the optimal regimen of repeated Cop 1 injections that will maximize the long term RGCs survival effect.

Figure 3:
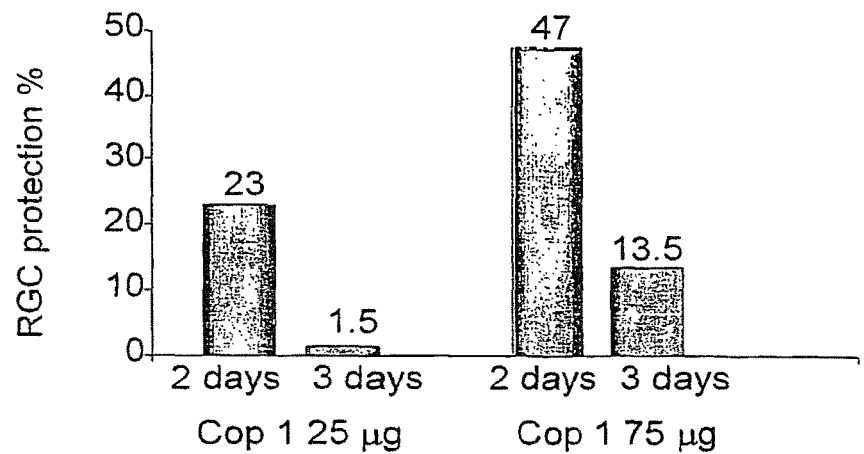
FIG. 3 shows that daily injections of Cop 1 repeated for three days at doses of 25 µg and 75 µg, cause loss of the neuroprotective effect on RGCs (at 25 µg, protection of 23% and 1.5% after 2 and 3 days, respectively; at 75 µg, protection of 47% and 13.5% after 2 and 3 days, respectively).

Cop 1 was originally developed as a therapy for multiple sclerosis (MS), an autoimmune disease characterized by unregulated T-cell activity against self-peptides of the CNS. Cop 1 is given to MS patients once a day at a dosage of 20 mg per patient by subcutaneous injections. We examined if daily injections of Cop 1 repeated for several days can maintain the neuroprotective effect on RGCs. Mice were immunized with Cop 1 daily for two or three days (Cop 1, 25 µg/mouse and 75 µg/mouse). The results, presented in FIG. 3, show that daily injections of Cop 1 repeated for two days, give neuroprotection on RGCs and better protection is achieved with 75 µg Cop 1, while immunization during three consecutive days cause loss of the neuroprotective effect on RGCs.

Figure 4:
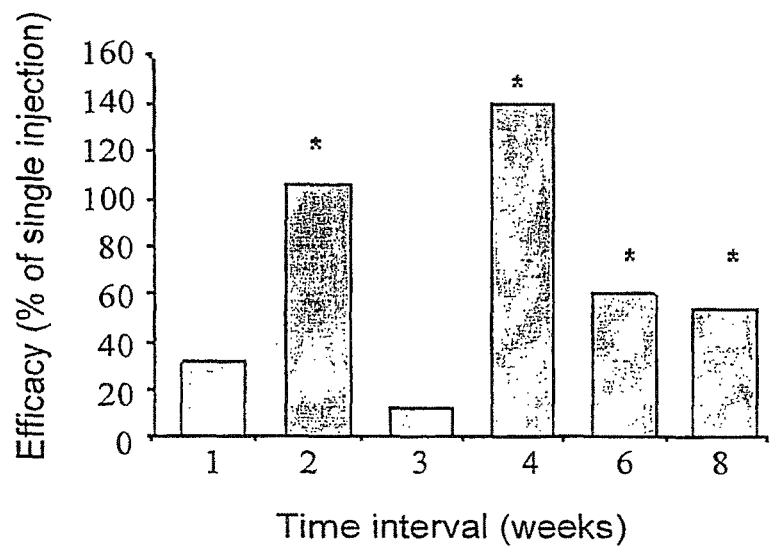
FIG. 4 shows the efficacy of two repeated injections of Cop 1 (75 µg/mouse), injected at different time intervals (1, 2, 3, 4, 6, 8, weeks). The neuroprotective effect of the treatment on RGCs is represented as % of a single injection of Cop 1 (75 µg/mouse), injected 7 days before induction of glutamate toxicity. This single injection was determined as positive control and performed in each experiment. * represents statistically significant difference (t-test, p<0.05) versus the non-treated group.
Figure 5:
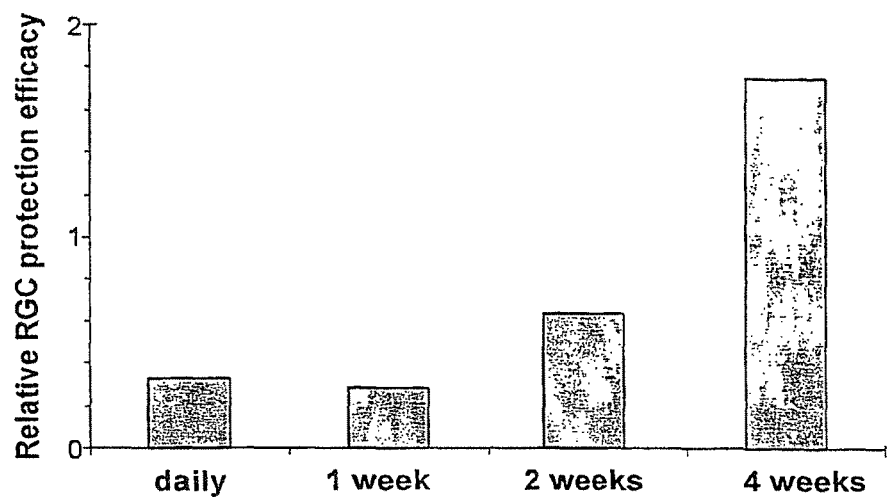
FIG. 5 shows the efficacy of three repeated injections of Cop 1 (75 µg/mouse) injected at different time intervals (daily, 1, 2, 4, weeks). The neuroprotective effect of the treatment on RGCs is represented as % of a single injection of Cop 1 (75 µg/mouse), injected 7 days before induction of glutamate toxicity. This single injection was determined as positive control and performed in each experiment.

To determine the vaccination regimen (best time interval) that produces the optimal degree of neuroprotection, three repeated Cop 1 injections were administered to mice at different time intervals ranging from daily to monthly. In one experiment, the mice received two 75 µg Cop 1 injections at intervals of 1, 2, 3, 4, 6 and 8 weeks. In another experiment, the mice received three repeated 75 µg Cop 1 injections daily or at intervals of 1, 2, and 4 weeks. The results are shown in FIGS. 4 and 5, respectively. The neuroprotective effect of the treatment is represented as % of a single injection of Cop 1 (75 µg/mouse) injected 7 days before glutamate toxicity was induced. This single injection was determined as positive control and was performed in each experiment. As shown in FIGS. 4 and 5, a 4-week interval between Cop 1 injections (75 µg/mouse) had the highest neuroprotective efficacy. It is striking that daily administration of Cop 1, the regimen used as therapy for multiple sclerosis, provides poor neuroprotection.

The results using the glutamate toxicity model showed that the regimen of repeated injections of Cop 1 may lead to a sustained neuroprotective effect. Based on these results, the optimal neuroprotective effect in mice was found to be repeated 75 μg injections of Cop 1 at 4 week intervals.

Example 2

Correlation Between the Cellular Immune Response to Cop 1 Vaccination and the Neuroprotective Effect Two ex vivo markers correlate with the efficacy—the T cell stimulation index and interferon-γ (IFN-γ). The stimulation index indicates the extent to which Cop-1-responsive T cells are present in the lymphocyte population. IFN-γ secretion is characteristic of T cells of the "Th1" subtype. These markers thus provide a means of profiling the cellular immune response.

The correlation between the neuroprotective effect and the cellular immune response to Cop 1 vaccination was thus determined by in vitro evaluation of T-cell proliferation and the level-profile of cytokine secretion.

The effect of Cop 1 vaccination was examined by isolating splenic lymphocytes from mice immunized with different doses of Cop 1 (25, 75 and 225 μg/mouse), 7, 14, 21 and 28 days after immunization, and measuring the proliferative response of the splenocytes to Cop 1 by [$^3$H]thymidine incorporation, and the induction of cytokine production (IFN-γ) by ELISA assay.

Figure 6:
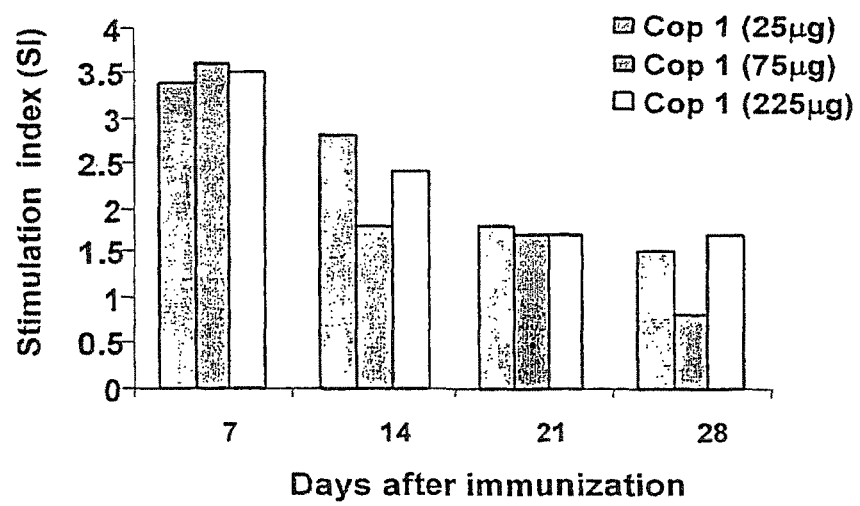
FIG. 6 shows proliferation of splenocytes from mice following immunization with different doses of Cop 1 (25 µg, 75 µg, 225 µg). The results after 7, 14, 21 and 28 days are expressed as stimulation index (SI), where SI is the mean cpm of cells incubated in vitro with Cop 1 divided by the mean cpm of cells incubated in vitro without Cop 1.

Uptake of labeled thymidine by splenocytes represents proliferation of specific T-cells to Cop 1, following Cop 1 vaccination. The results in FIG. 6 are expressed as stimulation index (SI), where SI is the mean cpm of cells incubated in vitro with the antigen (Cop 1) divided by the mean cpm of cells incubated in vitro without the antigen (Cop 1). A positive response was defined as SI>2. A single injection of Cop 1 resulted in increased SI after 7 days for the three doses. After 14 days, only marginal proliferation of T-cells was seen for injection of 25 and 225 μg Cop 1 and less proliferation for injection of 75 μg Cop 1. The SI decreased after 21 and 28 days, meaning that the splenocytes proliferation in response to Cop 1 had abated. These results corroborate the glutamate toxicity results that showed that the neuroprotective efficacy decreases with time.

Figure 7:
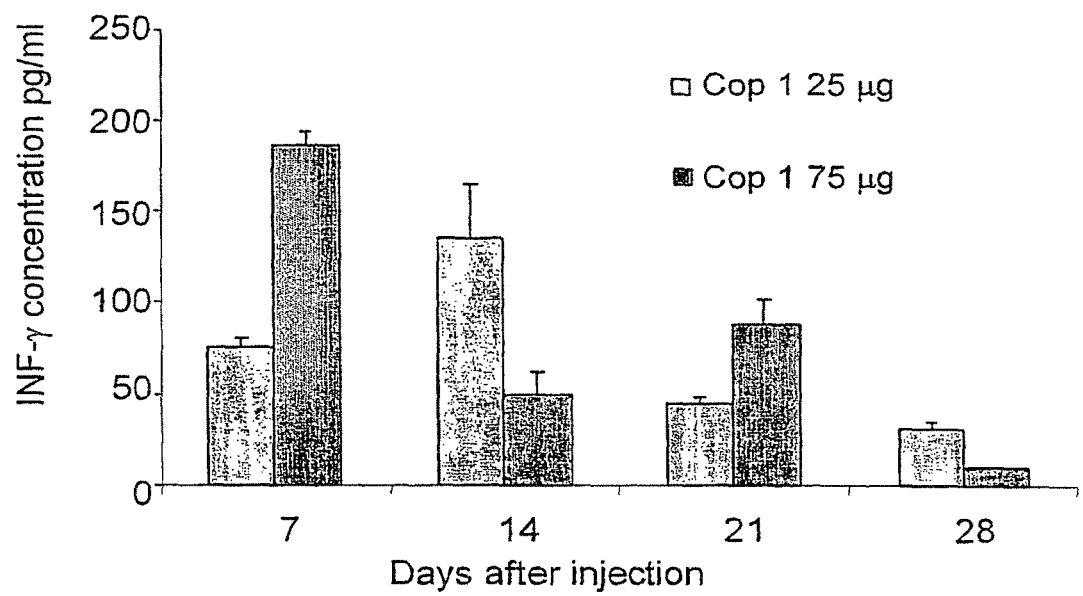
FIG. 7 shows INF-γ secretion from stimulated splenocytes 7, 14, 21 or 28 days after immunization with 25 µg or 75 µg Cop 1.

Secretion of INF-γ by stimulated splenocytes was measured by ELISA (R&D Systems). As shown in FIG. 7, the highest level of INF-γ secretion from splenocytes was observed 7 days after Cop 1 immunization (25 and 75 μg/mouse). The levels of INF-γ declined after 14, 21 and 28 days. These results are in agreement with the results obtained for neuroprotective efficacy and T-cell proliferation.

Neuroprotective efficacy was correlated with IFN-γ secretion, similar to the effect shown in FIG. 1. In contrast, T-cell proliferation remains high under daily injections of Cop-1. This result shows that while Cop-1 responsive T cells are still present, the loss of IFN-γ secretion indicates a shift in the predominant phenotype of the cells; this is accompanied by a loss of neuroprotective efficacy. It therefore appears that neuroprotection is associated with IFN-γ secretion.

The above animal results are in line with the observation that daily injections of Copaxone® to MS patients leads to a Th2 type response (Vieira et al., 2003). Thus, the daily regimen of Cop-1 should not be expected to confer neuroprotection and is not the regimen of choice for Huntington's disease; vaccinations spaced at wider intervals are more likely to prove effective.

Example 3

In Vivo Animal Test System for Huntington's Disease

The beneficial effect of Cop 1 vaccination was examined for exertion of neuroprotective effects using the HD R6/2 transgenic mice test system. R6/2 transgenic mice over express the mutated human huntingtin gene that includes the insertion of multiple CAG repeats (Mangiarini et al., 1996). These mice show progressive behavioral-motor deficits starting as early as 5-6 weeks of age, and leading to premature death at 10-13 weeks. The symptoms include low body weight, clasping, tremor and convulsions (Carter et al., 1999).

Two different doses of Cop 1 vaccination were tested, 75 μg Cop 1/mouse (n=13) and 150 μg Cop 1/mouse (n=11), that were injected when the mice were 45 days old and every 4 weeks thereafter. A third group (n=12) was vaccinated with 75 μg Cop 1/mouse on day 60 of age and every 4 weeks thereafter. The control group (n=17) was injected with PBS starting on day 45 of age and every 4 weeks thereafter. Motor neurological functions were evaluated using the rotarod performance test, which assesses the capacity of the mice to stay on a rotating rod. For this test, mice were placed on a rod rotating at 2 rpm: the time until the mouse falls off the rotating rod (best of three attempts, up to 180 sec for each trial), is used as the measure of animal motor-function. Each mouse was tested twice weekly and the two scores averaged.

Figure 8:
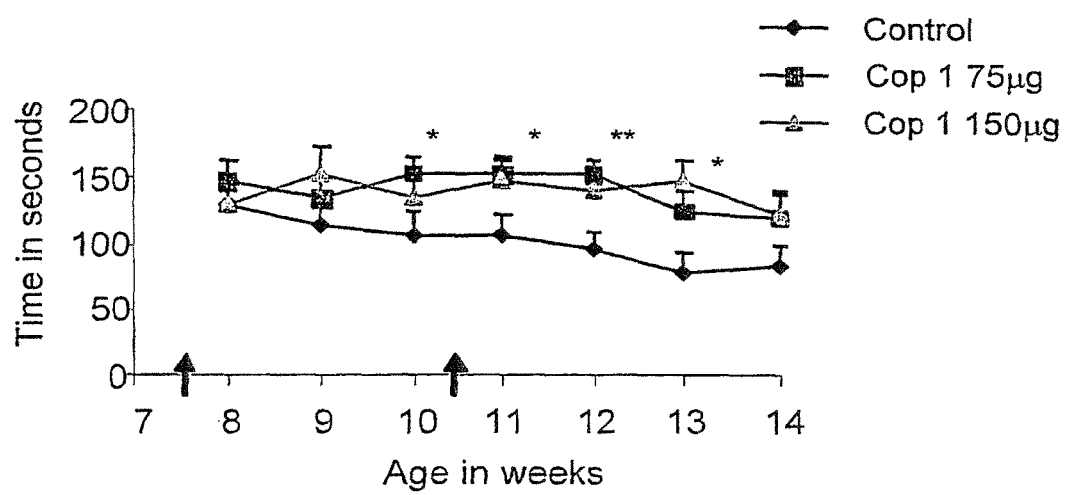
FIG. 8 is a graph showing the rotarod performance of HD R6/2 transgenic mice after vaccination with 75 µg or 150 µg Cop 1.

The results are shown in FIG. 8. Each point on the graphs represents the average group score for each week (SEM indicated by error bar). The arrows on the x-axis represent the timing of Cop 1 (or PBS) injections. The results show that vaccination with Cop 1, either 75 μg/mouse or 150 μg/mouse, starting on day 45 of age, produced a significant improvement in motor performance during the follow-up period of 8 to 14 weeks. However, vaccination with 75 μg Cop 1/mouse starting on day 60 of age had no significant effect (data not shown).

Figure 9:
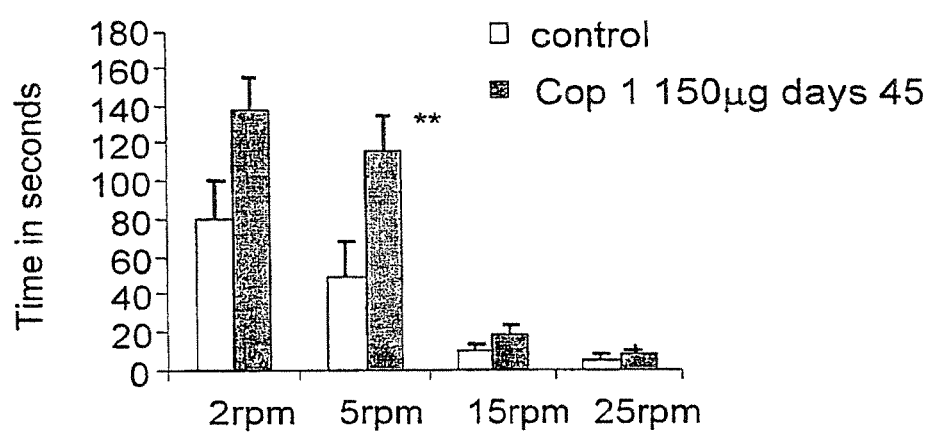
FIG. 9 shows the rotarod performance of HD R6/2 transgenic mice following vaccination with 150 µg Cop 1, at different speeds of rotation (2, 5, 15 and 25 rpm).

Control and Cop 1 vaccinated HD R6/2 transgenic mice (150 μg/mouse) were subjected to rotarod performance test on day 45 using four different speeds: 2, 5, 15 and 25 rpm. FIG. 9 shows that the improvement in rotarod performance following Cop 1 vaccination is dependent on the speed of rotation. Significant better performance of the twelve-week old vaccinated HD R6/2 mice compared to non-treated HD R6/2 control mice was most clearly apparent using 5 rpm rotarod speed.

The effect of Cop 1 vaccination on weight loss of HD R6/2 transgenic mice was tested on the three groups. Mice were weighed twice a week at the same time during the day. No effect on body weight was observed following vaccination on day 45 or day 60 using either 75 μg/mouse or 150 μg/mouse Cop 1 compared to the control group.

It could also be observed that Cop 1 vaccination significantly delayed mortality and onset of disease of HD R6/2 mice. The effect of Cop 1 vaccination on survival of the HD transgenic mice is shown in Table 1. Statistical comparisons of survival were made by ANOVA followed by the Fisher's least significant difference test.

TABLE 1

Effect of Cop 1 vaccination on survival of HD R6/2 mice

|  | Control | Cop 1 75 μg/mouse day 45 | Cop 1 150 μg/mouse day 45 | Cop 1 75 μg/mouse day 60 |
| --- | --- | --- | --- | --- |
| Survival (days) | 103 ± 2.5 | 110 ± 2.7* | 101 ± 3.5 | 108 ± 1.6 |
| Onset of disease | 78 ± 3.8 | 89 ± 4.5 (p = 0.065) | 91 ± 3.7* | 79 ± 5.6 |

In conclusion, the results of Examples 1 and 2 show that Cop 1 vaccination attenuates neuronal cell death induced by exposure to elevated levels of the excitotoxic neurotransmitter glutamate, and that the neuroprotective effect is dependent upon activation and proliferation of T-cells specific to Cop 1 that secrete INF-γ (Th1). The neuroprotective effect is short-lived, unless maintained by a boosting regime—it is build up by 7 days post immunization, and is then reduced due to activation of regulatory cells which terminate the response. The Cop 1 dose found to be the most active in the animal models was 75 µg Cop 1/mouse, that translate to a human adult dose of 20 mg on a mg/m² basis. The optimal regimen for neuroprotection in mice was monthly injection, both in the glutamate toxicity model and to reduce the rate of motor function deficits and to improve life expectancy in the HD R6/2 transgenic mice, as shown in Example 3. Thus, for human use, neuroprotective Cop 1 vaccination should be administered in doses spaced at least one month apart, preferably 4-6 weeks apart, more preferably every 5 or 6 weeks.

Example 4

Human Clinical Trials for Huntington's Disease

The primary objective of the human study is to evaluate the tolerability, safety and immunological response of the serial administration of 20 mg or 2×20 mg dose of Cop 1 (Copaxone®) or another Cop 1 formulation) versus placebo, in patients suffering from Huntington's disease. The secondary objective of the study is to evaluate the neurological course of patients with HD disease following administration of Cop 1, by measuring the following neurological clinical parameters: Unified Huntington's Disease Rating Scale (UHDRS) and Total Motor Scale (TMS).

Eligible patients (female and male, 18-70 years old, symptomatic patients with clinically diagnosed HD and a confirmatory family history of HD) will receive one administration of placebo (40 mg mannitol/injection) and three administrations of Copaxone® (20 mg/ml subcutaneously or 2×20 mg/ml subcutaneously, 1 in each arm) at 6 weeks intervals between administrations. Blood samples for immunological profile analysis will be taken at screening and prior to first injection. Each administration of Copolymer 1 will be followed by a series of blood sampling to determine the immunological profile on days 7, 14, 28 and just prior to next injection and termination.

UHDRS is a research tool that has been developed by the Huntington Study Group (HSG). The purpose of the scale is to allow the researchers to grade the symptoms of HD in a way that allows them to make accurate comparisons between individual patients, and to better chart the course of the disease in patients. The scale is divided into a number of different sub-scales, including the Total Motor Score 4 (TMS-4). In the human trial, a primary end-point is the change over a period of time, e.g. one-year period, in the TMS-4 subscale of the UHDRS, the standard rating scale for trials in HD. The pre-determined and end-points of the trial (such as UHDRS scores) are compared for the patients on Copaxone and the one may assume the possibility that the drug can be said to have had some kind of impact on Huntington's disease.

Section II: Vaccination with Autoantigen or Cop 1 Protects Against β-Amyloid and Glutamate Toxicity Neurodegenerative diseases differ in etiology but are propagated similarly. In the experiments in this section, we show that neuronal loss caused by intraocular injection of aggregated β-amyloid was significantly greater in immuno-deficient mice than in normal mice. The neurodegeneration was attenuated or augmented by elimination or addition, respectively, of naturally occurring $CD4^+CD25^+$ regulatory T cells (Treg). Vaccination with retina-derived antigens or with Copolymer-1, but not with β-amyloid, reduced the ocular neuronal loss. In mouse hippocampal slices, microglia encountering activated T cells overcame the cytotoxicity of aggregated β-amyloid. These findings support the concept of "protective autoimmunity", show that a given T cell-based vaccination is protective at a particular site irrespective of toxicity type, and suggest that locally activated T cells induce a microglial phenotype that helps neurons withstand the insult Alzheimer's and other neurodegenerative diseases might be arrested or retarded by vaccination with Cop-1 or related compounds or by treatment with compounds that weaken Treg suppression.

In the experiments below, we showed that intraocular injection of the aged (aggregated) form of the β-amyloid peptide 1-40 ($A\beta_{1-40}$) causes loss of retinal ganglion cells (RGCs), similarly to the effect of toxic concentrations of glutamate. We further showed that in both cases the destructive effect could be attenuated either by elimination of naturally occurring $CD4^+CD25^+$ regulatory T cells (Treg) or by evoking an immune response directed against antigens derived from the tissue's own constitutively expressed proteins (rather than against the threatening compound itself). The therapeutic effect could be reproduced by passive transfer of T cells directed against the same self-antigens.

Materials and Methods—Section II (vii) Animals.

Mice were handled according to the Association for Research in Vision and Ophthalmology (ARVO) resolution on the use of animals in research. Male C57BL/6J wild type, BALB/c/OLA wild type, and nude mice, all specific pathogen-free and aged between 8 and 13 weeks, were supplied by the Animal Breeding Center of The Weizmann Institute of Science (Rehovot, Israel) under germ-free conditions. The mice were housed in a light- and temperature-controlled room and matched for age in each experiment. Mice were anesthetized by i.p. administration of ketamine (80 mg/kg; Ketaset, Fort Dodge, Iowa) and xylazine (16 mg/kg; Vitamed, Ramat-Gan, Israel). Prior to tissue excision, the mice were killed with a lethal dose of pentobarbitone (170 mg/kg; C. T. S., Kiryat Malachi, Israel).

(viii) Antigens.

Bovine interphotoreceptor retinoid-binding protein (IRBP) was purified from retinal extracts by affinity chromatography on Con A as described (Pepperberg et al., 1991). Bovine S-antigen (arrestin) was prepared from the Con A column flowthrough by the method of Buczylko and Palczewski (Palczewski et al., 1994) as modified by Puig et al. (1995). Whole retinal homogenate (WRH) was prepared from syngeneic retinas homogenized in PBS. Ovalbumin (OVA), Con A, and β-amyloid peptide 1-40 ($A\beta_{1-40}$)) were purchased from Sigma-Aldrich, St. Louis, Mo. The $A\beta_{(1-40)}$ peptide was dissolved in endotoxin-free water, and β-amyloid aggregates were formed by incubation of $A\beta_{(1-40)}$, as described (Ishii et al., 2000). Glatiramer acetate (Copaxone®; Cop-1) was purchased from Teva Pharmaceuticals Ltd. (Petach Tikva, Israel).

(ix) Immunization.

Adult mice were immunized with IRBP (50 µg), S-antigen (50 µg), $A\beta_{1-40}$ (50 µg), WRH (600 µg), or Cop-1 (75 µg), each emulsified in an equal volume of CFA (Difco, Detroit, Mich.) containing *Mycobacterium tuberculosis* (5 mg/ml; Difco). The emulsion (total volume 0.15 ml) was injected s.c. at one site in the flank. Control mice were injected with PBS in CFA or with PBS only.

(x) Labeling of RGCs in Mice.

Labeling was carried out as described in Materials and Methods, Section I (v).

(xi) Induction of Toxicity by Injection of Glutamate or Aggregated $A\beta_{1-40}$.

The right eyes of anesthetized C57BL/6J or BALB/c/OLA mice were punctured with a 27-gauge needle in the upper part of the sclera and a Hamilton syringe with a 30-gauge needle was inserted as far as the vitreal body. Each mouse was injected with a total volume of 1 µl of PBS containing L-glutamate (400 nmol; Sigma-Aldrich) or aggregated $A\beta_{1-40}$ (50 µM; Sigma-Aldrich).

(xii) Assessment of Retinal Ganglion Cell Survival.

At the end of the experimental period the mice were given a lethal dose of pentobarbitone (170 mg/kg). Their eyes were enucleated and the retinas were detached, prepared as flattened whole mounts in 4% paraformaldehyde in PBS, and labeled cells from four to six fields of identical size (0.076 mm$^2$) were counted (Schori et al., 2001b). The average number of RGCs per field was calculated for each retina. The number of RGCs in the contralateral (uninjured) eye was also counted, and served as an internal control.

(xiii) In-Situ Detection of Cell Death by Terminal Deoxynucleotidyl Transferase DNA (TUNEL).

Mice were killed 48 h after intraocular glutamate injection and their eyes were removed and processed for cryosectioning. Frozen sections were fixed in 3.7% formalin for 10 min at room temperature and washed twice with PBS. The sections were transferred to 100% methanol for 15 min at −20° C., washed twice for 5 min in ethanol 100%, 95% and 70% successively, and then incubated for 10 min with PBS. For permeabilization, proteases were digested with proteinase K for 20 min at room temperature. The open ends of the DNA fragments were labeled using an in-situ apoptosis detection kit (R&D Systems, Minneapolis, Minn.) according to the manufacturer's instructions. The labeled ends were detected using the fluorescein detection kit supplied with a streptavidin-fluorescein conjugate. The fluorescein-stained cells were visualized using a fluorescence microscope.

(xiv) Preparation of Splenocytes Depleted of CD4$^+$CD25$^+$ Regulatory T Cells.

Splenocytes prepared by a conventional procedure were incubated with rat anti-mouse phycoerythrin(PE)-conjugated CD25 antibody, and this was followed by incubation with anti-PE beads (Becton-Dickinson, Bactlab Diagnostic, Haifa, Israel). After being washed, the splenocytes were subjected to AutoMacs (Miltenyi Biotec, Bergisch Gladbach, Germany) with the "deplete sensitive" program. Recovered populations were analyzed by FACSsort (Becton Dickinson, Franklin Lakes, N.J.) (Kipnis et al., 2002a).

(xv) Preparation of Activated Naïve T Cells.

Lymph nodes (axillary, inguinal, superficial cervical, mandibular, and mesenteric) and spleens were harvested and mashed. T cells were purified (enriched by negative selection) on T cell columns (R&D Systems). The enriched T cells were incubated with anti-CD8 microbeads (Miltenyi Biotec), and negatively selected CD4$^+$ T cells were incubated with PE-conjugated anti-CD25 antibodies (30 µg/10$^8$ cells) in PBS/ 2% fetal calf serum. They were then washed and incubated with anti-PE microbeads (Miltenyi Biotec) and subjected to magnetic separation with AutoMACS. The retained cells were eluted from the column as purified CD4$^+$CD25$^+$ cells (Treg). The negative fraction (effector T cells, Teff), consisting of CD4$^+$CD25$^-$ T cells, was further activated for 4 days, in medium containing 5×10$^5$ cells/ml, with spleen-derived APC (irradiated with 3000 rad), and 0.5 µg/ml anti-CD3 antibodies, supplemented with 100 units of mouse recombinant IL-2 (mrIL-2; R&D Systems).

(xvi) Preparation of Antigen-Specific Activated Lymphocytes from Immunized Mice.

Ten days after immunization, the mice were killed and their draining lymph nodes were excised and pressed through a fine wire mesh. The washed lymphocytes (2×10$^6$ cells/ml) were activated with the relevant antigens (IRBP$_{1-20}$ or aggregated $A\beta_{1-40}$, each at 10 µg/ml) in stimulation medium containing RPMI supplemented with L-glutamine (2 mM), 2-mercaptoethanol (5×10$^{-5}$ M), penicillin (100 IU/ml), streptomycin (100 IU/ml), and autologous mouse serum 1% (vol/vol). After incubation for 48 h at 37° C., 90% relative humidity, and 7% $CO_2$ the lymphocytes were washed with PBS, counted, and injected intraperitoneally into autologous mice not more than 1 h after intravitreal injection of a toxic dose (50 µM) of aggregated $A\beta_{1-40}$.

(xvii) Microglial Cultures.

Microglia were purified from the cerebral cortices of newborn (day 0) BALB/c/OLA mice, as described (Butovsky et al., 2001). IFN-γ (20 ng/ml; R&D Systems), β-amyloid (Sigma-Aldrich; aggregated $A\beta_{1-40}$ 25 µM), or activated T cells (1.5×10$^5$ per well) were added to the culture medium for 12 h. After treatment, microglia were washed three times with PBS and prepared for application on hippocampal slices.

(xviii) In-Vitro Model of Hippocampal Slices.

BALB/c/OLA mice, aged 8-10 days, were decapitated and their brains were rapidly removed under sterile conditions and placed in ice-cold preparation medium consisting of minimum essential medium (MEM; Gibco, Carlsbad, Calif.) with 1% L-glutamine (Gibco) at pH 7.35. The frontal pole was removed and the brains were cut into 350-µm horizontal slices on a vibratome (Pelco, Redding, Germany), beginning at the ventral surface. Slices containing the hippocampi were cultured on Falcon cell culture inserts, pore size 0.4 µm (Becton Dickinson), in 6-well plates. The cultivation medium contained 50% MEM, 25% Hanks balanced salt solution (Gibco), 25% normal horse serum, 2% glutamine, 10 µg/ml insulin-transferrin-sodium selenite supplement (Boehringer Mannheim, Mannheim, Germany), 2.64 mg/ml glucose (Braun, Melsungen, Germany), 0.1 mg/ml streptomycin, 100 U/ml penicillin, and 0.8 µg/ml vitamin C (all from Sigma-Aldrich). The organotypic hippocampal slice cultures (OHSCs) were incubated at 35° C. in a humidified atmosphere with 5% $CO_2$ for 24 h, during which time the slices were either left untreated or treated with 4×10$^5$ microglia per well. Tissue loss was assessed by addition of propidium iodide (PI) (5 µg/ml; Sigma) to the medium for 30 min at the end of the incubation period. Excess PI was then washed away with cultivation medium, and the slices were prepared for microscopy and visualized. To quantify neural cell death in the OHSCs, PI intensity in each slice was assessed by use of Image-Pro software (Media Cybernetics, Carlsbad, Calif.). PI staining intensity for a specific treatment was compared to that of the untreated control, using a two-tailed Student's t-test.

Example 5

Figure 10A:
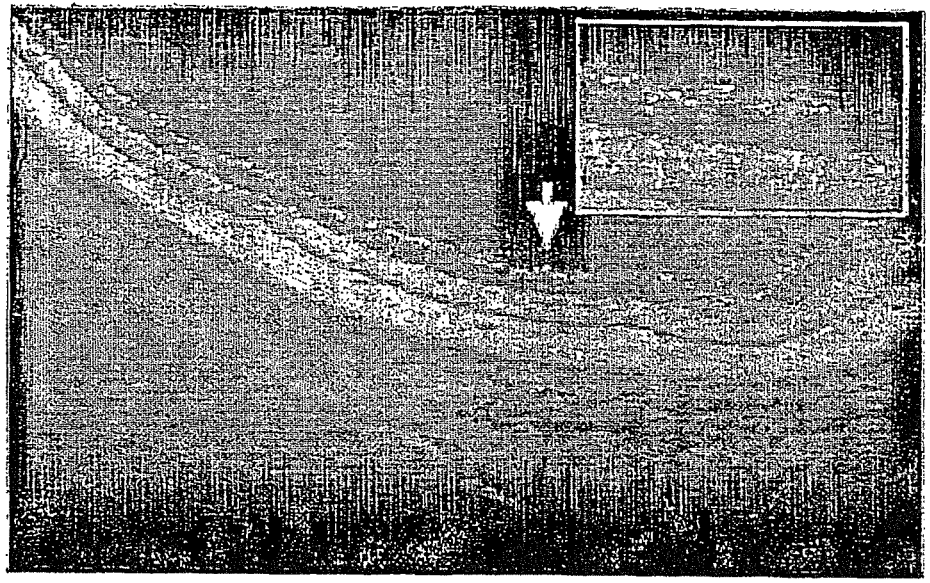
FIGS. 10A-10D show that immunization of mice with retinal proteins protects retinal ganglion cells against glutamate toxicity. (A) TUNEL-positive cells in the RGC layers of C57Bl/6J mice 48 h after intravitreal injection of a toxic dose of glutamate. Sections (20 µm thick) were subjected to TUNEL staining, counterstained with propidium iodide, and viewed by confocal microscopy to detect TUNEL-positive cells. A confocal image of a representative retina is shown. The arrow indicates TUNEL-positive cells in the RGC layer. Scale bar=200 µm. (B) C57Bl/6J mice were immunized in the flank with 600 µg of whole retinal homogenate (WRH) emulsified in CFA supplemented with 5 mg/ml of *Mycobacterium tuberculosis*. Six days later the mice were injected intravitreally with glutamate (400 nmol). One week later surviving RGCs were counted. Significantly more RGCs survived in mice immunized with WRH/CFA than in mice immunized with PBS/CFA. The figure shows the results, expressed as neuronal loss relative to the RGC population of normal retinas, of one representative experiment out of two independent experiments (n=6-8 mice per experiment in each group; P<0.0001, two-tailed Student's t-test). (C, D) In another set of experiments mice were immunized in the flank with interphotoreceptor-binding protein (IRBP; 50 µg) or S-antigen (50 µg) emulsified in CFA supplemented with 5 mg/ml of *Mycobacterium tuberculosis*. Control mice were immunized with PBS in CFA. Significantly more neurons were lost in the PBS/CFA immunized group than in the IRBP/CFA immunized group ($P<0.0001$; two-tailed Student's t-test; n=6-8 mice in each group) or in the S-antigen-immunized group ($P<0.0001$; n=6-8 mice per group).
Figure 10B:
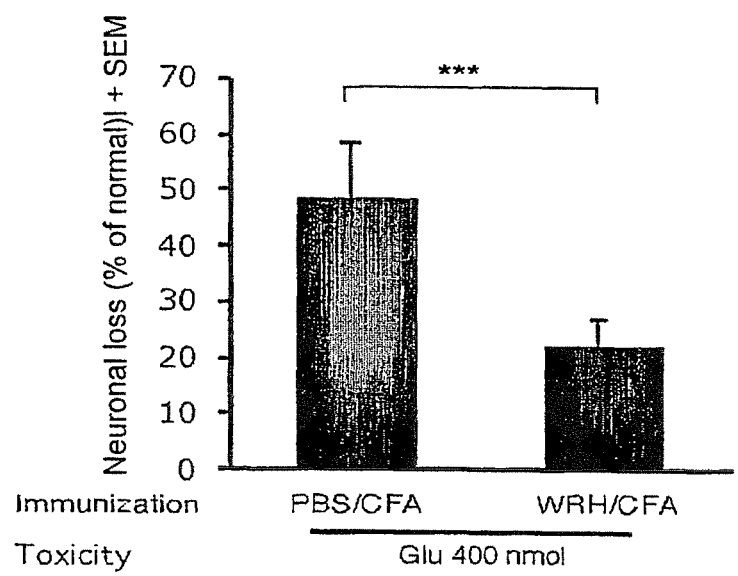

Retinal Proteins can Evoke a Protective T Cell-Based Response to Glutamate Intoxication We have shown previously that mice of different genetic backgrounds differ in their ability to resist injurious conditions (Schori et al., 2001b; Kipnis et al., 2001; Schori et al., 2002). The differences were attributed, at least in part, to strain-related variations in the ability to manifest a T cell-dependent protective response (Kipnis et al., 2001). In view of the observed failure of myelin proteins to protect mice against glutamate toxicity in the eye and the successful protection against glutamate toxicity in rats by retinal proteins (Schori et al., 2001b; Mizrahi et al., 2002) we were interested in examining whether immunization of mice with retinal proteins would improve their neuronal survival after exposure to glutamate toxicity, and if so, whether the same vaccination would be effective against other threatening compounds (such as aggregated β-amyloid) injected into the same site. Glutamate (400 nmol) was injected into the right eyes of C57BL/6J mice, and 48 h later we examined retinal cryosections subjected to terminal deoxynucleotidyl transferase biotin-dUTP nick end labeling (TUNEL). Apoptotic cell death was observed in the RGC layer (FIG. 10A). When mice of this strain were vaccinated with a homogenate of whole retinal proteins (WRH) in CFA 6 days before being injected with a toxic dose of intraocular glutamate (400 nmol), examination 1 week later disclosed survival of significantly more RGCs than that seen in age- and strain-matched control mice injected with PBS emulsified in CFA (2239.7±153.3 and 1480.6±176.2, respectively, P<0.0001; two-tailed Student's t-test). This finding indicated that vaccination with the retinal components had increased the ability of the immunized mice to withstand glutamate toxicity. FIG. 10B shows that the vaccination significantly reduced RGC loss, expressed as a percentage of the numbers in normal controls (mean±SEM; FIG. 10B).

Figure 10C:
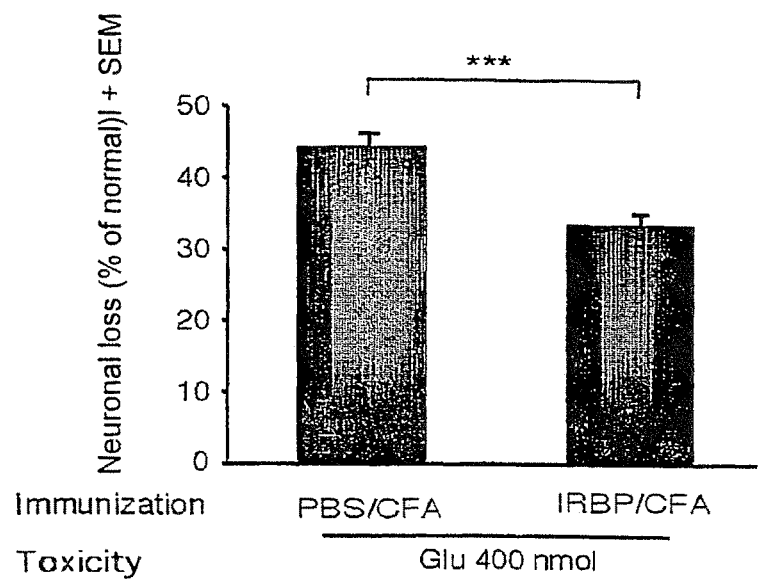
Figure 10D:
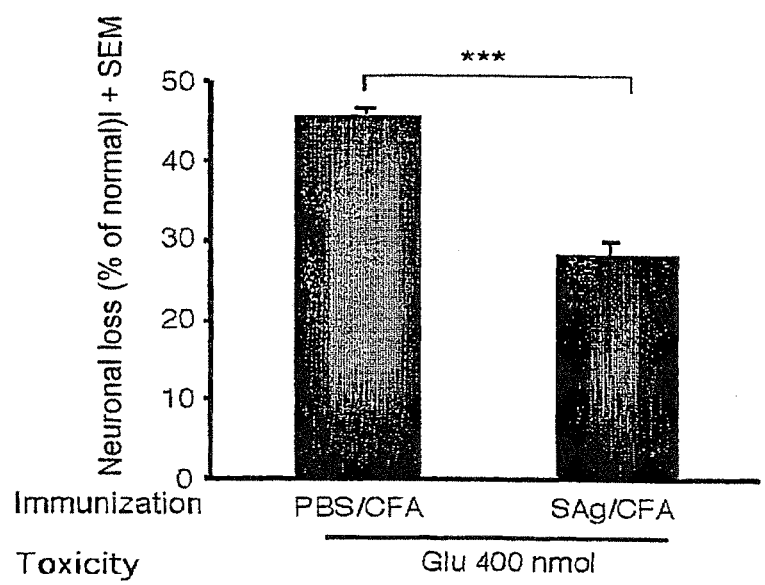

In light of the above results, and to further test our hypothesis that the evoked protection against glutamate toxicity is an outcome of a T cell-mediated response to the retinal self-antigens, we examined whether immunization with the specific eye-resident antigens interphotoreceptor retinoid-binding protein (IRBP) or S-antigen (retinal arsenin), rather than with the retinal homogenate, can protect RGCs against glutamate toxicity Immunization of C57BL/6J mice, 10 days before glutamate injection, with IRBP emulsified in CFA, resulted in survival of significantly more RGCs than in glutamate-injected C57BL/6J mice immunized with PBS/CFA (1996±49.53 and 1649±43, respectively, P<0.0008; two-tailed Student's t-test; FIG. 10C) Immunization with the retinal self-antigen S-antigen in CFA resulted in a similar increase in neuronal survival relative to immunization with PBS/CFA (2160±38 and 1648±37, respectively, P<0.0001; two-tailed Student's t-test; FIG. 10D). For ease of comparison, the results in the figure are presented as the loss of neurons expressed as a percentage of the number of RGCs in strain-matched normal retinas.

It should be emphasized that the retinal self-proteins IRBP and S-antigen, both of which are capable of causing uveitis in susceptible mice (Caspi et al., 1990a; Caspi et al., 1990b) but were used here for purposes of protection, are not intended for development as a therapeutic vaccination; this is purely an experimental paradigm, used here for proof of concept, that supports our previous contention that the same T cells can be both protective and destructive, and that their actual effect is a reflection of the tissue context, the quantity of T cells, and the timing of their activities in the tissue (Mizrahi et al., 2002; Hauben et al., 2001; Fisher et al., 2001).

Example 6

Ability to Withstand the Toxicity of β-Amyloid is T Cell-Dependent

Having shown that the physiologically relevant antigen for protection against neurotoxicity is not the toxic compound itself (glutamate) but a self-antigen that resides in the site of damage, we then examined whether the same vaccination might be beneficial against different toxic self-compounds provided that the toxicity is restricted to the same site. We tested this hypothesis by examining the effect of the vaccination on the toxicity of aggregated β-amyloid. Aggregated β-amyloid ($A\beta_{1-40}$) (5 or 50 µM) was injected into the right eyes of C57BL/6J mice. This model (intraocular injection of β-amyloid) was chosen not because of the supposed association of this compound with the optic neuropathy in Alzheimer's disease (Bakalash et al., 2002; Schwartz, 2004), but because β-amyloid is capable of causing RGC death (Jen et al., 1998), and therefore its use allows us to further explore the concept of antigenic specificity. Surviving RGCs were counted 1 or 2 weeks after ocular injection of aggregated β-amyloid. After 1 week, the numbers of viable RGCs were 2257±77 (5 µM injection) and 2071±30 (50 µM injection), and after 2 weeks they were 2062±41 (5 µM) and 1952±21 (50 µM). A total of 3445±57 neurons were counted in naïve mice. Under the same experimental conditions, toxicity caused by injection of the vehicle alone did not affect more than 5% of RGCs in the normal retina. FIG. 11A shows the β-amyloid-induced neuronal loss expressed as a percentage of the average number of RGCs in normal wild-type retina. FIGS. 11B and 11C show representative photomicrographs of whole-mounted retinas excised from mice after intraocular injection of PBS and aggregated $A\beta_{1-40}$, respectively.

To determine whether the ability of naïve mice to withstand the toxicity of aggregated $A\beta_{1-40}$ is T cell-dependent, we compared RGC survival in wild type and nude (nu/nu) BALB/c/OLA mice 2 weeks after intraocular injection of aggregated $A\beta_{1-40}$ (50 µM). Significantly more neurons survived in the injected wild-type mice (2316±53) than in their T cell-deficient counterparts (1779±147; P<0.01). The choice of BALB/c/OLA mice for this experiment was based on a previous observation that the T cell-dependent ability of this strain to withstand the consequences of CNS injury is significantly better than that of C57BL/6J mice (Schori et al., 2001b; Kipnis et al., 2001; Kipnis et al., 2004), and thus any differences resulting from the absence of T cells would be more easily detectable in the BALB/c/OLA mice. FIG. 11D shows neuronal loss as a percentage of the number of neurons in normal retinas. FIGS. 11E and 11F show representative micrographs of retinas from wild-type and nude mice, respectively, after intraocular injection of aggregated $A\beta_{1-40}$. These results support the contention that the strain is a factor in the ability of neural tissue to withstand ocular toxicity, and show that strain-related differences in that respect are related not to the type of insult but to the ability to harness a well-controlled T cell-dependent immune response.

Figure 12A:
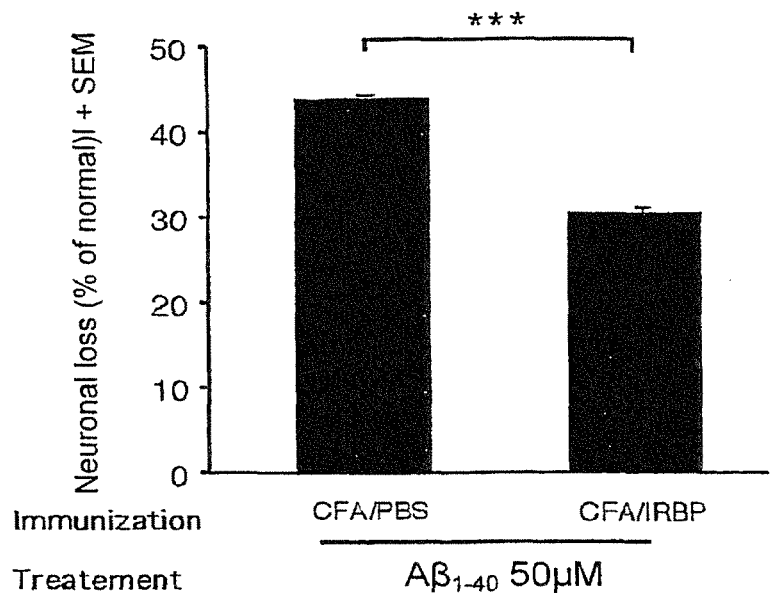
FIGS. 12A-12B show that immunization with an antigen residing in the site of toxicity rather than with the toxic agent itself protects against aggregated $A\beta_{1-40}$ toxicity in C57Bl/6J mice. C57Bl/6J mice were immunized in the flank with interphotoreceptor-binding protein (IRBP; 50 µg) in CFA, the β-amyloid peptide (1-40, non-aggregated) (50 µg) in CFA, or PBS in CFA. In all cases, CFA was supplemented with 5 mg/ml of *Mycobacterium tuberculosis*. Ten days later the mice were injected intravitreally with a toxic dose of aggregated $A\beta_{1-40}$ (50 µM), and after 10 days their retinas were excised and the surviving RGCs counted. (A) Significantly fewer RGCs were lost in C57BL6/J mice immunized with IRBP/CFA than in matched controls treated with PBS/CFA ($P<0.0008$, two-tailed Student's t-test). (B) The mean number of surviving RGCs in mice immunized with native β-amyloid peptide in CFA did not differ significantly from that in mice injected with PBS/CFA.
Figure 12B:
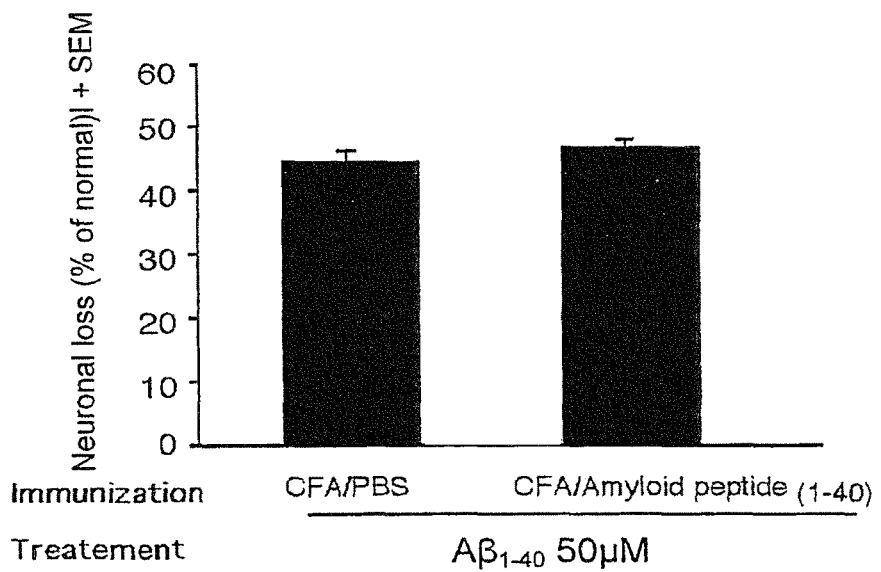

To further test our working hypothesis that the T cell specificity needed for neuroprotection is directed not against the threatening compound but against self-antigens that reside in the site of the lesion, we subjected C57BL/6J mice to intraocular toxicity of aggregated $A\beta_{1-40}$ and then immunized them with the IRBP-derived peptide (which, as in the case of glutamate toxicity (FIG. 10C), is protective against the intraocular toxicity of aggregated $A\beta_{1-40}$). After vaccination, the loss of RGCs induced by aggregated $A\beta_{1-40}$ was significantly smaller than that observed in mice immunized with PBS/CFA (RGC survival was 2307±62 for IRBP/CFA and 1840±56 for PBS/CFA; FIG. 12A). We also immunized C57BL/6J mice with the non-aggregated (non-toxic) form of the β-amyloid peptide before injecting them intraocularly with $A\beta_{1-40}$. After vaccination with β-amyloid/CFA, the loss of RGCs induced by aggregated $A\beta_{1-40}$ did not differ significantly from that observed in mice immunized with PBS/CFA (RGC survival was 1743±55 and 1831±45, respectively; FIG. 12B).

Figure 13A:
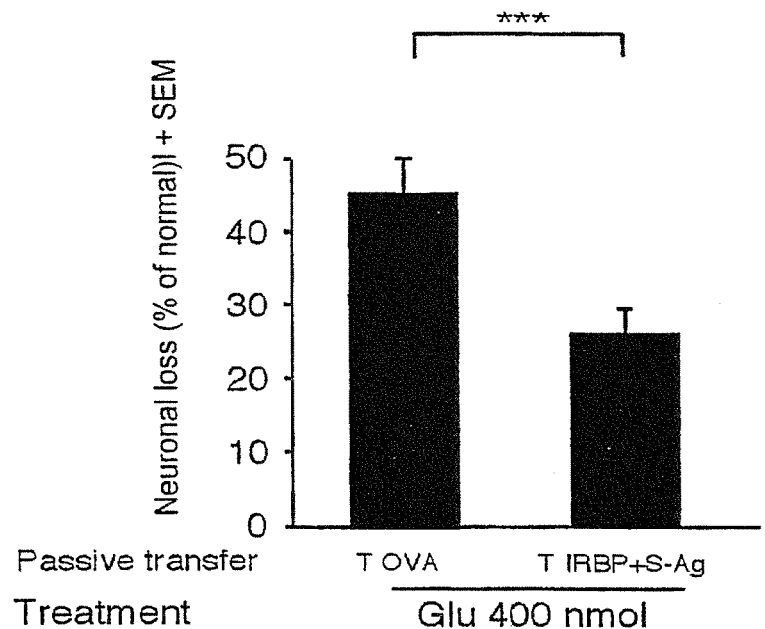
FIGS. 13A-13B show that passive transfer of activated splenocytes from mice immunized with dominant retinal antigens into naïve mice results in protection. (A) Wild-type C57Bl/6J mice were immunized in the hind foot pads with a combination of interphotoreceptor-binding protein (IRBP) and S-antigen (50 µg each) or 50 µg OVA emulsified in CFA supplemented with 5 mg/ml of *Mycobacterium tuberculosis*. Ten days later draining lymph nodes were excised and pooled, cell suspensions were prepared, and the cells were counted. Cells were activated ex-vivo by stimulation with their specific antigens for 48 h, and the activated T cells were then injected i.p. into naïve C57Bl/6J mice. T cells specific to IRBP+S-antigen were injected at a dose of $1.2\times10^7$ T cells in PBS. Within 1 h of passive T cell transfer the mice received an intravitreal injection of glutamate (400 nmol), and surviving retinal ganglion cells (RGCs) were counted 1 week later. Significantly fewer RGCs survived in mice that received OVA-specific T cells than in mice that received T cells specific to IRBP+S-antigen ($P<0.001$; two-tailed Student's t-test). There was no difference between mice that received OVA-specific T cells and naïve mice in the numbers of RGCs that survived the glutamate injection (n=4-6 mice per group). (B) Mice were injected intravenously with $8\times10^6$ activated T cells directed either to IRBP or to β-amyloid peptide (1-40, non-aggregated). One hour after this passive T-cell transfer, the mice were injected with a toxic dose of aggregated $A\beta_{1-40}$. Two weeks later their retinas were excised and surviving RGCs counted. Neuronal loss in these mice was significantly decreased by transfer of T cells reactive to the IRBP ($P<0.005$, two-tailed Student's t-test), but was not significantly affected by transfer of T cells reactive to non-aggregated β-amyloid.

To verify that the observed vaccination-induced protection is T cell-dependent, we prepared primary T cells directed against IRBP and S-antigen or against IRBP only. After their activation ex vivo, the lymphocytes ($1.2 \times 10^7$ cells) were transferred into naïve C57BL/6J mice freshly exposed to toxicity of glutamate or aggregated $A\beta_{1-40}$. Significantly more RGCs survived in mice that received lymphocytes activated with IRBP+S-antigen than in mice immunized with lymphocytes activated by the non-CNS antigen OVA (2220±38 compared to 1652±56, P<0.001; two-tailed Student's t-test; FIG. 13A). RGC survival in mice that received OVA-activated T cells did not differ significantly from that in naïve mice injected with glutamate (1652.6±56 and 1535.6±74, respectively; not shown). Results are expressed as the percentage increase in neuronal survival relative to survival in control mice (FIG. 13A).

Figure 13B:
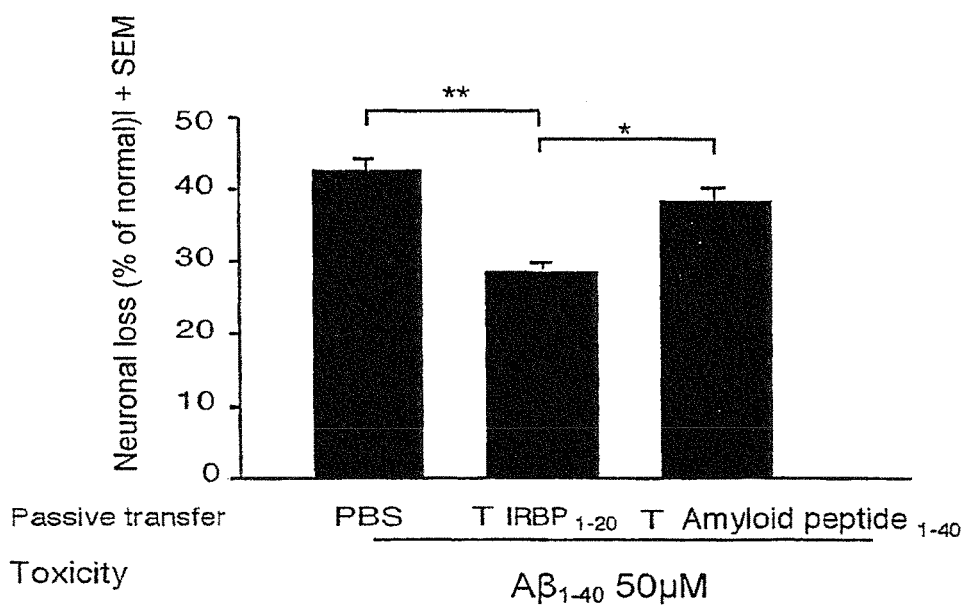

Similarly, T cells specific to IRBP or to non-aggregated $A\beta_{1-40}$ obtained from immunized mice were prepared and activated ex vivo, and then passively transferred into C57BL/6J mice exposed to toxicity of aggregated $A\beta_{1-40}$. Passive transfer of the T cells activated with IRBP-derived peptide was beneficial in mice that were injected intraocularly with aggregated $A\beta_{1-40}$, as shown by the significantly smaller loss of RGCs in these mice than in normal control mice (FIG. 13B). In contrast, in mice that received a passive transfer of T cells specific to non-aggregated $A\beta_{1-40}$, the loss of RGCs after intraocular injection with a toxic dose of aggregated $A\beta_{1-40}$ differed only slightly from that in mice treated with PBS.

These findings confirmed that the protection achieved by active vaccination with IRBP (FIG. 12A) against the toxicity of aggregated $A\beta_{1-40}$ was T cell-mediated. The failure of T cells directed to the aggregated $A\beta_{1-40}$ itself to confer protection is in line with observations in our laboratory that microglia, upon encountering aggregated $A\beta_{1-40}$, fail to express MHC class II (MHC-II). Consequently, such microglia fail to present β-amyloid to the T cells, with the result that even if β-amyloid-specific T cells home to the CNS they will not be locally activated (Butovsky et al., unpublished observations). To fight β-amyloid toxicity, a more appropriate choice would therefore be antigens that reside in the site and can be presented to homing T cells.

Figure 14:
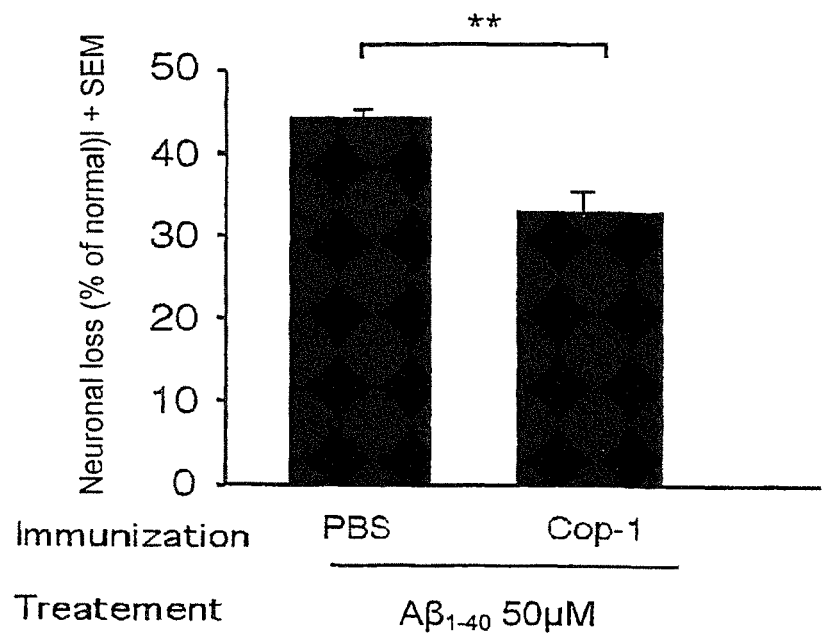
FIG. 14 shows that active immunization with Cop-1 protects against $A\beta_{1-40}$ toxicity. C57Bl/6J mice were immunized with Cop-1, 6 days before being injected intravitreally with aggregated $A\beta_{1-40}$. Two weeks later their retinas were excised and the surviving cells counted. Significantly fewer RGCs were lost in mice immunized with Cop-1 than in matched controls treated with PBS ($P<0.001$, two-tailed Student's t-test).

The results summarized above suggest that an appropriate choice for vaccination in order to fight β-amyloid toxicity would be antigens that reside in the site of degeneration and that can be presented to the homing T cells. Because of the diversity of the human histocompatibility complex, vaccination with self-antigens cannot be assumed to be safe for therapeutic purposes. In searching for a safe vaccine we examined the efficacy of vaccination with the synthetic antigen glatiramer acetate (Cop-1) (Schori et al., 2001b; Kipnis et al., 2000) which was previously shown to act as a partial agonist or an altered peptide ligand in mimicking the effect of a wide-range of self-reactive T cells without causing an autoimmune disease (Schori et al., 2001b). Significant protection against toxicity of aggregated β-amyloid was obtained by vaccinating C57BL/6J mice with Copolymer 1 seven days before they were injected intraocularly with a toxic dose of aggregated $A\beta_{1-40}$ (FIG. 14). RGC survival in Cop-1-treated and PBS-treated mice was 1939±80 and 1617±43, respectively P<0.01; two-tailed Student's t-test.

Example 7

Naturally Occurring Regulatory CD4$^+$CD25$^+$ T Cells Restrict the Body's Ability to Withstand β-Amyloid Toxicity in the Retina The above observation that in the absence of intervention the ability of mice to withstand the toxicity of aggregated $A\beta_{1-40}$ is T-cell dependent (FIG. 11) prompted us to investigate whether the ability of the neural tissue to spontaneously withstand the toxicity of aggregated β-amyloid is suppressed by the naturally occurring regulatory CD4$^+$CD25$^+$ T cells (Treg), as described in the case of other CNS insults (Kipnis et al., 2002a; Schwartz and Kipnis, 2002a). If so, elimination or weakening of such control might serve as an additional way to harness the autoimmune T cells needed for protection against β-amyloid-associated neurodegenerative conditions.

Figure 15A:
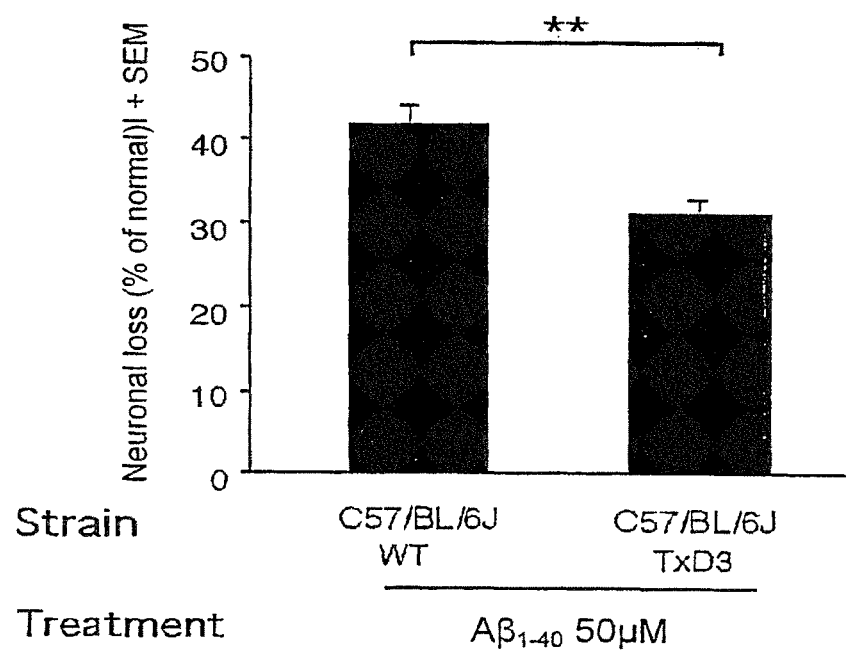
FIGS. 15A-15C show that more neurons survive aggregated $A\beta_{1-40}$ intoxication in mice devoid of naturally occurring regulatory CD4+CD25+ T cells than in naïve mice. (A) C57Bl/6J mice devoid of Treg as a result of thymectomy 3 days after birth (TXD3 mice) were injected intravitreally with a toxic dose of $A\beta_{1-40}$ at the age of 12 weeks. Significantly fewer RGCs were lost in the TXD3 mice than in age-matched normal controls ($P<0.001$; two-tailed Student's t-test; n=6-8 mice per group). (B) BALB/c/OLA nu/nu mice were replenished with $4.5\times10^7$ splenocytes from spleens devoid of Treg or from whole spleens of BALB/c/OLA mice. After injection of aggregated $A\beta_{1-40}$, significantly fewer RGCs were lost in nu/nu mice replenished with splenocytes devoid of Treg than in matched wild-type controls ($P<0.05$; two-tailed Student's t-test). In both groups, significantly fewer RGCs were lost than in untreated nu/nu mice injected with aggregated $A\beta_{1-40}$ ($P<0.001$; two-tailed Student's t-test). In each experiment, the number of RGCs counted in eyes not exposed to aggregated $A\beta_{1-40}$ toxicity was taken as the normal baseline value. The results of one experiment out of two are presented. (C) Semi-quantitative RT-PCR analysis of Foxp3 expression. mRNA was extracted from freshly isolated Teff and Treg. The housekeeping gene β-actin was used for quantitative analysis. The results shown are from one representative experiment out of five.
Figure 15B:
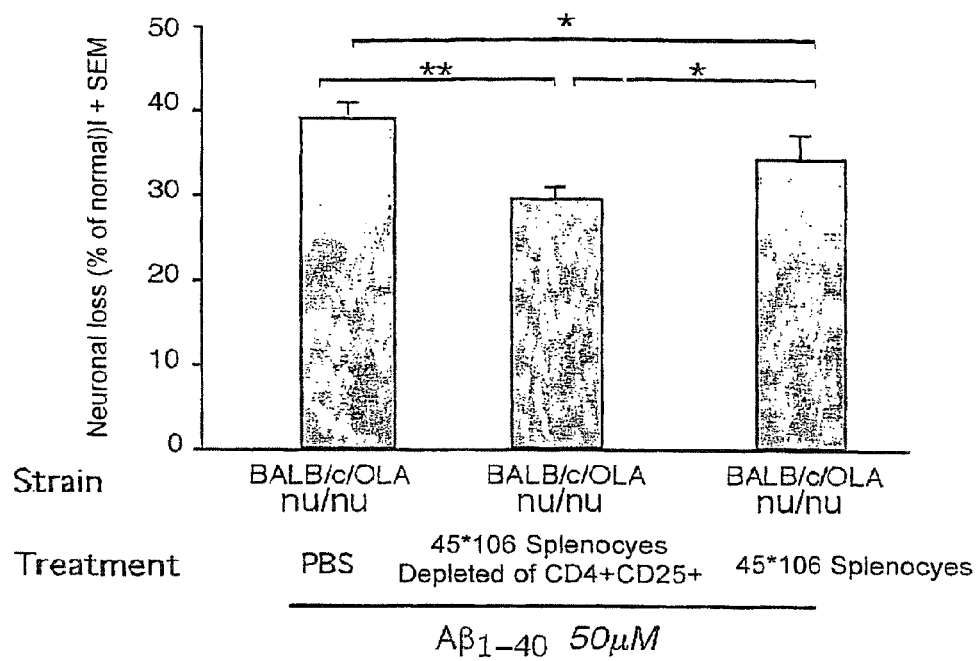
Figure 15C:
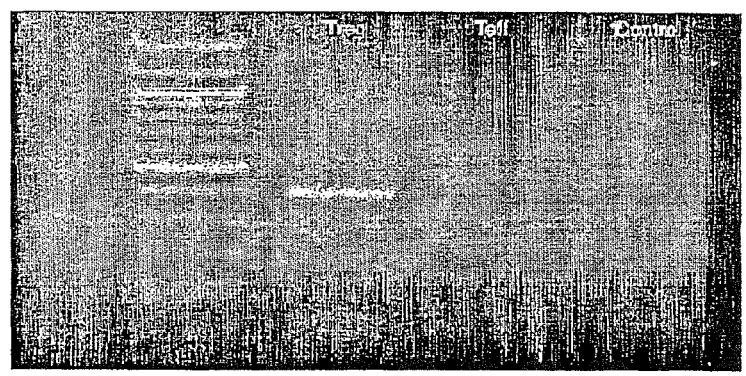

We therefore examined whether the ability of the murine neural tissue to withstand the toxicity of aggregated $A\beta_{1-40}$ could be boosted by removal of Treg. In adult C57BL/6J mice that had undergone thymectomy 3 days after birth (a procedure that results in Treg depletion [Sakaguchi et al., 2001; Seddon, 2000]), significantly more RGCs survived exposure to aggregated $A\beta_{1-40}$ than in matched non-thymectomized controls (2251±53 and 1918±94, respectively; P<0.01; two-tailed Student's t-test; FIG. 15A). In a complementary experiment, nude mice of the BALB/c/OLA strain were replenished with $4.5 \times 10^7$ wild-type splenocytes from which the Treg population had been removed ex vivo. As controls, we used nude mice replenished with the same number of splenocytes, which were obtained from whole spleens of wild-type mice and therefore contained both Treg and effector T cells (Teff). Three days after replenishment, the recipient mice were injected with a toxic dose of aggregated $A\beta_{1-40}$, and surviving RGCs were counted 2 weeks later. Significantly fewer RGCs died in the mice replenished with splenocytes depleted of Treg than in mice replenished with a normal splenocyte population; in both groups, however, fewer RGCs died than in the group of untreated nu/nu mice injected with aggregated $A\beta_{1-40}$ (RGC survival was 2412±61, 2246±101, and 2080±56, respectively; FIG. 15B). These findings suggest that Treg normally down-regulate the ability of the neural tissue to spontaneously withstand aggregated $A\beta_{1-40}$ toxicity. PCR testing for Foxp3 expression, found to be associated with Treg (Khattri et al., 2003), confirmed that the Treg were Foxp3-positive whereas CD4$^+$CD25$^-$ T cells were Foxp3-negative (FIG. 15C).

Example 8

T Cells Prevent Microglia from Developing an Inflammatory Cytotoxic Phenotype

Figure 16A:
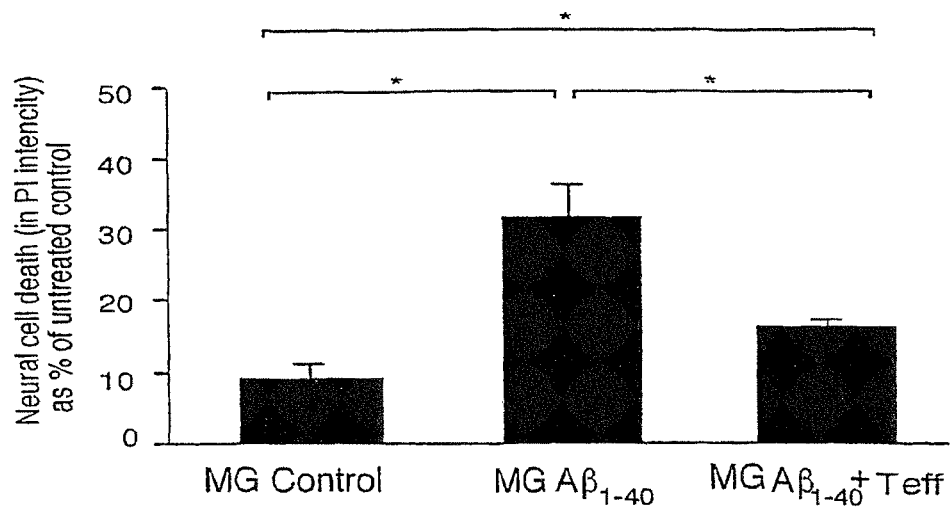
FIGS. 16A-16B show death of neural cells in rat organotypic hippocampal slice cultures 24 h after treatment with microglia incubated with aggregated $A\beta_{1-40}$ with and without activated T cells. OHSCs were obtained from BALB/c/OLA mice. Immediately after sectioning, the slices were co-cultured for 24 h with microglia that had been pre-incubated (12 h) with aggregated $A\beta_{1-40}$ alone or with a combination of aggregated $A\beta_{1-40}$ and activated Teff (A). Control slices were treated with naïve microglia or were left untreated. Twenty-four hours after co-culturing of microglia and brain slices, the slices were stained with propidium iodide (PI) (a fluorescent dye that stains only dead cells) and analyzed by fluorescence microscopy. (A) quantification of PI intensity, calculated as a percentage of the intensity measured in untreated control OHSCs (*$P<0.05$;  $P<0.01$, * $P<0.001$; two-tailed Student's t-test; n=6-8 slices per group). (B), selected photomicrographs of untreated control slices (1), slices incubated with untreated microglia (2), slices treated with microglia that were pre-incubated with aggregated $A\beta_{1-40}$ (3), and slices treated with microglia that had been exposed to aggregated $A\beta_{1-40}$ in conjunction with activated T cells (4).
Figure 16B:
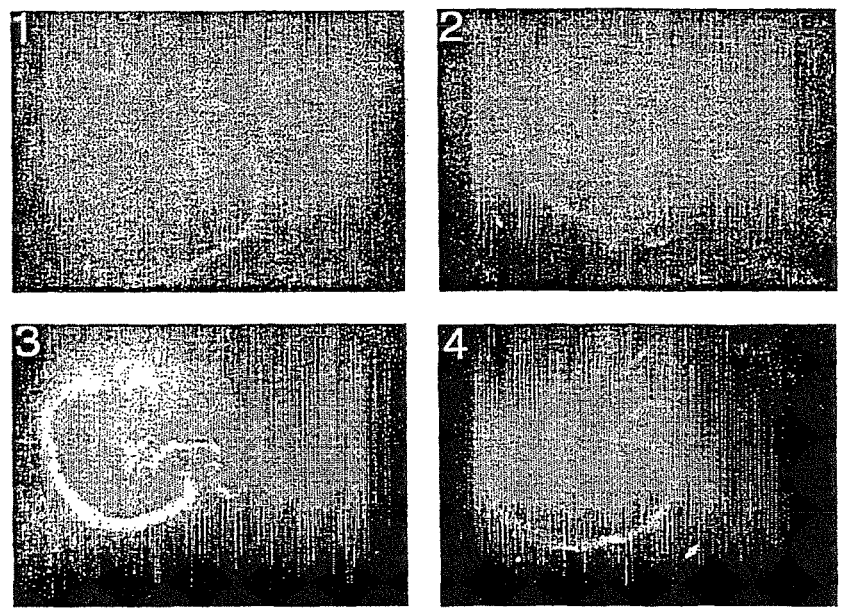

We have previously proposed that one way in which the autoimmune T cells help to fight off destructive self-compounds is by controlling the activity of microglia (Schwartz et al., 2003). Using organotypic hippocampal slice cultures (OHSCs), our group showed that after rat microglia are pretreated with aggregated $A\beta_{1-40}$ they become cytotoxic to neural tissue and their ability to express MHC-II is suppressed (Butovsky et al., unpublished observations). We therefore carried out an in-vitro experiment to determine whether murine microglia exposed to aggregated $A\beta_{1-40}$ also become cytotoxic, and if so, whether activated T cells can overcome the toxicity. After exposure of mouse microglia to aggregated $A\beta_{1-40}$, their addition to mouse OHSCs resulted in significantly more neuronal death than that seen in OHSCs that were untreated or were treated with naïve microglia (FIG. 16). The loss was significantly reduced, however, if the added microglia, at the time of their exposure to aggregated $A\beta_{1-40}$, had also been exposed to activated effector ($CD4^+CD25^-$) T cells (FIG. 16A). Representative micrographs of variously treated OHSCs and untreated controls are shown in FIG. 16B (1-4). These findings support the contention that exposure of microglia to activated T cells in suitably controlled amounts not only prevents the microglia from becoming cytotoxic, but also enables them to become neuroprotective. It should be noted that the microglial toxicity assayed in vitro does not reflect the lack of MHC-II expression, as this bioassay does not require antigen presentation.

Example 9

In Vivo Animal Test System for Alzheimer's Disease

The beneficial effect of Cop 1 vaccination can be examined for exertion of neuroprotective effects using the transgenic mice test system.

There are no spontaneous animal mutations with sufficient similarities to AD to be useful as experimental models. Various transgenic animal models for testing potential treatments for Alzheimer's disease are known. Models are known that are based on the ability to control expression of one or more of the three major forms of the human β-amyloid precursor protein (APP), APP695, APP751, and APP770, or subfragments thereof, as well as various point mutations based on naturally occurring mutations, such as the familial Alzheimer's disease (FAD) mutations at amino acid 717, and predicted mutations in the APP gene, as described in U.S. Pat. No. 6,717,031 and Johnson-Wood et al. (1997). A suitable model is, for example, the transgenic hAPP770/FAD717 mouse model.

To test the effect of Cop 1, a suitable formulation comprising Cop 1 is administered to the offspring of the transgenic mice or cells derived therefrom, and detecting or measuring an Alzheimer's disease marker in the transgenic mouse, or in cells derived from the transgenic mouse. In one preferred embodiment, the Alzheimer's disease marker is a behavior and the observed difference is a change in the behavior observed in the transgenic mouse to which the compound has been administered. This behavior may be behavior using working memory, behavior using reference memory, locomotor activity, emotional reactivity to a novel environment or to novel objects, and object recognition. For example, the behavior of the Cop 1-treated Alzheimer transgenic mouse model can be tested using the Morris water maze, as described (Postina et al., 2004). It is expected that the treated animals will exhibit an improvement in their behavior.

Discussion

The results of the present invention as described in Section II above suggest that in developing a therapeutic vaccination to counteract the toxicity caused by accumulation of aggregated $A\beta_{1-40}$ and other toxic agents such as glutamate, the same vaccine can be used provided that the toxic agents are all located, as is often the case, in the same site. In the mouse model used in Section II above, two neurotoxic self-compounds were injected into the eye, and protection against both of them was achieved by vaccination with the same antigens, namely peptides derived from proteins that reside in the eye. We interpret this finding as proof of principle that dominant self-antigens constitutively residing in a site of damage are the self-protective antigens against threatening conditions at this site. We further show that depletion of the naturally occurring $CD4^+CD25^+$ regulatory T cells (Treg) can increase the spontaneous response to such antigens and thus the ability to withstand the toxic effect of aggregated β-amyloid. As a therapeutic strategy, however, we propose vaccinating with Copolymer 1, a synthetic weak agonist of self-antigens (Schori et al., 2001b; Kipnis et al., 2000; Angelov et al., 2003; Ziemssen et al., 2002), rather than with the site-specific self-proteins themselves, because the former can be used as a protective vaccine without risk of inducing an autoimmune disease, a potential hazard associated with inherently inadequate control of autoimmunity (Schwartz, and Kipnis, 2002). As an alternative strategy, we propose the use of any manipulation that will weaken the activity of Treg (Kipnis et al., 2003).

Neurodegenerative disorders such as Parkinson's, Alzheimer's, Huntington's, prion, motor neuron diseases, and other devastating chronic neurodegenerative syndromes have several features in common, including the accumulation of self-proteins that have either become aggregated or undergone conformational changes (Perlmutter, 2002). In the case of Alzheimer's disease, accumulation of aggregated $A\beta_{1-40}$ is potentially a major cause of neuronal toxicity (Hardy and Selkoe, 2002). The present results support the contention that the β-amyloid peptide in its aggregated form (found in senile plaques) has a toxic effect in the CNS, not only because it is directly toxic to neurons (Jen et al., 1998; Carter and Lippa, 2001) but also because it apparently induces microglia to adopt a cytotoxic phenotype. In addition, the failure of β-amyloid vaccination to protect against β-amyloid-induced stress in the eye is in line with observations from our laboratory that cell-surface MHC-II expression is impaired in microglia encountering aggregated β-amyloid (Butovsky et al., unpublished observations).

In the past, it was generally assumed that because activated microglia are seen in the context of neurodegenerative diseases, these cells contribute to the ongoing degeneration (Qin et al., 2002). Accordingly, a substantial research effort was devoted to achieving their suppression.

The results in Section II above indicate that an alternative approach to the problem necessitates modulation of the microglial phenotype, thereby not only minimizing the risk carried by malfunctioning microglia but also exploiting microglial assistance in withstanding the destructive effects of aggregated $A\beta_{1-40}$ and other toxic agents associated with ongoing degeneration such as glutamate and oxidative stress. The phenotype acquired by microglia exposed to activated T cells is not destructive insofar as it does not produce inflammation-associated enzymes or promote redox imbalance (Schwartz et al., 2003). Thus, T cells that can be locally activated, irrespective of the identity of the antigen(s) residing in the damaged site, can trasform the adjacent microglial population from an enemy into a friend.

In the experiments described in Section II above, we observed strain-related differences in the ability of mice to withstand the toxicity of aggregated $A\beta_{1-40}$. The present results are also in line with our contention that naturally occurring $CD4^+CD25^+$ regulatory T cells constitutively control the ability to withstand neurodegenerative conditions. Although these cells are key participants in protection against autoimmune disease (Kohm et al., 2002), they limit the ability to fight degeneration in the CNS (Kipnis et al., 2002a). We have previously postulated that the presence of these cells reflects an evolutionary compromise between the need for autoimmune protection and the risk of developing an autoimmune disease because of inadequate control of the immune response (Kipnis et al., 2002a; Schwartz and Cohen, 2000), the latter being an outcome of the failure of Treg to display optimal suppressive activity (Kohm et al., 2002). In rats or mice devoid of Treg, the susceptibility to autoimmune disease development is increased, despite the benefit in terms of protection against injurious conditions Therefore, one of the aims of neuroprotective therapy is to weaken Treg. Thus, pharmacological intervention with a compound that mimics the physiological weakening (but not blocking) of Treg might provide a way to boost the T cell-based self-defense.

It was shown by our group that the same autoimmune T cells can be both supportive and destructive (Kipnis et al., 2002b). Accordingly, in animals that are inherently susceptible to autoimmune disease the protocol used for eliciting the T cell response critically affects the outcome. Thus, a strong adjuvant might lead to an autoimmune response whose benefit is offset by its persistence or intensity (Hauben et al., 2001). In such susceptible strains, however, autoimmune response to CNS might not be expressed early enough to be accommodated within the therapeutic window, or it might fail to meet other requirements, such as timely shut-off (Shaked et al., 2004a). Moreover, in susceptible strains devoid of immune cells (SCID) and thus lacking a T cell-based regulatory mechanism, passive transfer of encephalitogenic T cells causes EAE, but is not sufficient for conferring any neuroprotection (Kipnis et al., 2002b). In contrast, when $CD4^+CD25^+$ regulatory T cells are passively transferred into SCID mice (Kipnis et al., 2004b), they can have a protective effect similar to that of encephalitogenic T cells passively transferred into the wild type (Hauben et al., 2000a, 2000b; Moalem et al., 1999a). In animals that are inherently resistant to autoimmune diseases the likelihood that the spontaneously evoked response to a CNS injury will be destructive is very low; on the other hand, it might be too weak to be beneficial and need boosting. Thus, whether or not autoimmunity will be beneficial under severe conditions in susceptible strain is determined by both regulation and context.

For therapies capable of meeting the criteria of both resistant and susceptible strains without running the risk of negative side effects, the use of weak synthetic antigens such as Cop-1 or other related compounds deserves consideration. Such a strategy, unlike vaccination with a peptide derived from a toxic antigen such as β-amyloid, can potentially provide risk-free benefit. Moreover, the same safe antigen can be used for protection at different sites of degeneration, a situation that is often required in patients.

The results herein further support the contention that the way in which the body harnesses the immune system for protection against neurodegenerative conditions is via a T cell-dependent pathway. In addition, they strengthen the notion that in adopting a therapeutic approach to neurodegenerative diseases characterized by protein deposition, the antigen selected for vaccination should not be the disease-specific protein such as the aggregated $A\beta_{1-40}$ in Alzheimer's disease, Lewy bodies in Parkinson's disease, or prion protein (PrP) in prion disease (Dodart et al., 2003; White et al., 2003), but a peptide derived from an immunodominant self-protein that resides at the site of CNS damage, a cryptic self-peptide, or an altered self-peptide, but preferably a non-self peptide that cross-reacts weakly with self such as Copolymer 1 and Copolymer 1-related peptides and polypeptides.

The T cell-based vaccination described in Section II above protected mice from the neurodegenerative effects of existing aggregated $A\beta_{1-40}$. The proposed strategy does not argue against the possible benefit of antibodies specific to Aβ-amyloid (Dodart et al., 2003; Furlan et al., 2003; Mohajeri, et al., 2002) as long as the peptide used for vaccination is not encephalitogenic. The two approaches, rather than being mutually antagonistic, might complement one another.

Section III: Vaccination with Cop 1 for Treatment of Parkinson'S Disease

Parkinson's disease (PD) is a neurodegenerative movement disorder characterized by a progressive loss of dopaminergic neurons in the substantia nigra and depletion of the neurotransmitter dopamine in the striatum. The best model of PD to date is the 1-methyl-4-phenyl-1,2,3,6-tetrahydropyridine (MPTP) animal model. MPTP has been shown to induce parkinsonism both in man and non-human primates. The neurotoxicity produced by 1-methyl-4-phenylpyridinium ion ($MPP^+$), a metabolite of MPTP, which is intracellularly transported into dopaminergic neurons, is thought to mimic human PD and provides a good model for studying neuroprotection in PD. The beneficial effect of Cop 1 immunization is examined for exertion of neuroprotective effects using the MPTP mice test system or another suitable model for Parkinson's disease. Neuroprotective therapy for PD with Cop 1 can attenuate the neurodegenerative effects and the rate of disease progression.

Materials and Methods—Section III (xix) Animals.

Male mice of the C57BL/6J strain, aged 8-13 weeks, supplied by the Animal Breeding Center of The Weizmann Institute of Science (Rehovot, Israel), are handled according to the regulations formulated by the Institutional Animal Care and Use Committee (IACUC).

(xx) Reagents.

Cop 1 (median MW: 7,200 dalton) is from Teva Pharmaceutical Industries Ltd. (Petach Tikva, Israel). MPTP.HC1 (Sigma) is dissolved in 0.9% NaCl.

(xxi) Immunization.

For immunization, Cop 1 dissolved in PBS (100 μl) is injected SC at one site in the flank of the mice. Control mice are injected with vehicle only.

(xxii) MPTP Treatment.

Male SJL mice in different groups are treated with different schedules of MPTP to induce degenerative processes that vary in intensity and time-course, for example, 18-20 mg/kg MPTP.HCl (Sigma) in PBS injected intraperitoneally (i.p.) four times, at 2 h intervals, over 1 day, or 20 mg/kg MPTP injected s.c twice per day, over 2 days. Control mice are administered a corresponding volume of vehicle alone.

Example 10

Effect of Cop 1 in the Parkinson MPTP Rodent Model

Male C57BL/6J mice are injected i.p. with 20 mg/kg MPTP.HCl in PBS, four times, at 2-h intervals. Cop 1 (75 μg or 150 μg Cop 1/mouse in PBS) or PBS (control group) is administered to the MPTP-treated animals 12 h after the last MPTP administration.

The motor dysfunction in PD is due to a profound reduction in striatal dopamine content caused by the loss of dopaminergic nerve fibers in the striatum. Motor performance of MPTP-treated mice immunized with Cop 1 or injected with PBS is measured on a Rotarod, as previously described (Hunot et al., 2004). The rotarod performance test assesses the capacity of the mice to stay on a rotating rod. It can be expected that immunization with Cop 1 will display improvement of motor functions on the Rotarod (increased Rotarod time) compared to control mice.

Other PD parameters related to neuroprotection can be carried out one week or more after immunization such as stereological quantification of dopamine neuron number and optical density measurement of dopamine fiber loss using immunostaining for dopamine transporter (DAT) and tyrosine hydroxylase (TH).

REFERENCES

Angelov D N, Waibel S, Guntinas-Lichius O, Lenzen M, Neiss W F, Tomov T L, Yoles E, Kipnis J, Schori H, Reuter A, Ludolph A, Schwartz M. (2003). Therapeutic vaccine for acute and chronic motor neuron diseases: implications for amyotrophic lateral sclerosis. Proc. Natl. Acad. Sci. U.S.A. 100(8):4790-4795.

Bakalash S, Kipnis J, Yoles E, Schwartz, M. (2002) Resistance of retinal ganglion cells to an increase in intraocular pressure is immune-dependent. Invest. Ophthalmol. Vis. Sci. 43: 2648-2653.

Benner E J, Mosley R L, Destache C J, Lewis T B, Jackson-Lewis V, Gorantla S, Nemachek C, Green S R, Przedborski S, Gendelman H E. (2004) Therapeutic immunization protects dopaminergic neurons in a mouse model of Parkinson's disease. Proc Natl Acad Sci USA. 101:9435-40.

Bomstein Y, Marder J B, Vitner K, Smirnov I, Lisaey G, Butovsky O, Fulga V, Yoles E. (2003) Features of skin-coincubated macrophages that promote recovery from spinal cord injury. J. Neuroimmunol. 142:10-16.

Butovsky O, Hauben E, Schwartz M. (2001) Morphological aspects of spinal cord autoimmune neuroprotection: colocalization of T cells with B7-2 (CD86) and prevention of cyst formation. Faseb J 15:1065-1067.

Carter R J, Lione L A, Humby T, Mangiarini L, Mahal A, Bates G P, Dunnett S B, Morton A J. (1999) Characterization of progressive motor deficits in mice transgenic for the human Huntington's disease mutation, J. Neurosci. 19(8): 3248-3257.

Carter R J and Lippa C F. (2001) Beta-amyloid, neuronal death and Alzheimer's disease. Curr. Mol. Med. 1: 733-737.

Caspi R R, Chan C C, Leake W C, Higuchi M, Wiggert B and Chader G J. (1990a) Experimental autoimmune uveoretinitis in mice. Induction by a single eliciting event and dependence on quantitative parameters of immunization. J. Autoimmun. 3: 237-246.

Caspi R R, Chan C C, Wiggert B, Chader G J (1990b) The mouse as a model of experimental autoimmune uveoretinitis (EAU). Curr Eye Res 9 Suppl: 169-174.

Conway K A, Harper J D, Lansbury P T (2000). Fibrils formed in vitro from α-synuclein and two mutant forms linked to Parkinson's disease are typical amyloid. Biochemistry. 39: 2552-2563.

Dauer W, Przedborski S. (2003) Parkinson's disease: mechanisms and models. Neuron 39: 889-909.

DiFiglia M, Sapp E, Chase K O, Davies S W, Bates G P, Vonsattel J P, Aronin N. (1997). Aggregation of huntingtin in neuronal intranuclear inclusions and dystrophic neurites in brain. Science. 277: 1990-1993.

Doble A. (1999) The role of excitotoxicity in neurodegenerative disease: implications for therapy. Pharmacol. Ther. 81: 163-221.

Dodart J C, Bales K R, Paul S M. (2003) Immunotherapy for Alzheimer's disease: will vaccination work? Trends Mol. Med. 9: 85-87.

Fisher J, Levkovitch-Verbin H, Schori H, Yoles E, Butovsky O, Kaye J F, Ben-Nun A, Schwartz M. (2001) Vaccination for neuroprotection in the mouse optic nerve: implications for optic neuropathies. J. Neurosci. 21: 136-142.

Fridkis-Hareli M, Aharoni R, Teitelbaum D, Arnon R, Sela M, Strominger J L. (1999) Binding motifs of copolymer 1 to multiple sclerosis- and rheumatoid arthritis-associated HLA-DR molecules. J Immunol. 162(8):4697-4704.

Furlan R, Brambilla E, Sanvito F, Roccatagliata L, Olivieri S, Bergami A, Pluchino S, Uccelli A, Comi G, Martino G. (2003) Vaccination with amyloid-beta peptide induces autoimmune encephalomyelitis in C57/BL6 mice. Brain 126: 285-291.

Gutekunst C A, Levey A I, Heilman C J, Whaley W L, Yi H, Nash N R, Rees H D, Madden J J, Hersch S M. (1995) Identification and localization of huntingtin in brain and human lymphoblastoid cell lines with anti-fusion proteins antibodies. Proc Natl Acad Sci USA 92(19): 8710-8714.

Hardy J, Selkoe D J. (2002) The amyloid hypothesis of Alzheimer's disease: progress and problems on the road to therapeutics. Science. 297: 353-356.

Hauben E, Butovsky O, Nevo U, Yoles E, Moalem G, Agranov G, Mor F, Leibowitz-Amit R, Pevsner E, Akselrod S, Neeman M, Cohen I R, Schwartz M.

Hauben E, Nevo U, Yoles E, Moalem G, Agranov E, Mor F, Akselrod S, Neeman M, Cohen I R, Schwartz M. (2000b) Autoimmune T cells are neuroprotective in spinal cord injury. Lancet 355:286-287.

Hauben E, Agranov E, Gothilf A, Nevo U, Cohen A, Smirnov I, Steinman L, Schwartz M (2001) Posttraumatic therapeutic vaccination with modified myelin self-antigen prevents complete paralysis while avoiding autoimmune disease. J Clin Invest 108:591-599.

Hauben E, Schwartz M. (2003) Therapeutic vaccination for spinal cord injury: helping the body to cure itself, Trends Pharmacol Sci. 24(1):7-12.

Hunot S, Vila M, Teismann P, Davis R J, Hirsch E C, Przedborski S, Rakic P, Flavell R A. (2004) JNK-mediated induction of cyclooxygenase 2 is required for neurodegeneration in a mouse model of Parkinson's disease. Proc Natl Acad Sci USA 101(2):665-70.

Ishii K, Muelhauser F, Liebl U, Picard M, Kuhl S, Penke B, Bayer T, Wiessler M, Hennerici M, Beyreuther K, Hartmann T, Fassbender K (2000) Subacute NO generation induced by Alzheimer's beta-amyloid in the living brain: reversal by inhibition of the inducible NO synthase. Faseb J 14:1485-1489.

Jen L S, Hart A J, Jen A, Relvas J B, Gentleman S M, Garey L J, Patel A J. (1998) Alzheimer's peptide kills cells of retina in vivo. Nature 392: 140-141.

Khattri R, Cox T, Yasayko S A, Ramsdell F. (2003) An essential role for Scurfin in CD4+CD25+ T regulatory cells. Nat. Immunol. 4: 337-342.

Kipnis J, Yoles E, Porat Z, Cohen A, Mor F, Sela M, Cohen I R, Schwartz M. (2000), T cell immunity to copolymer 1 confers neuroprotection on the damaged optic nerve: possible therapy for optic neuropathies, Proc Natl Acad Sci USA. 97:7446-7451.

Kipnis J, Yoles E, Schori H, Hauben E, Shaked I, Schwartz M. (2001) Neuronal survival after CNS insult is determined by a genetically encoded autoimmune response. J Neurosci. 21(13):4564-71.

Kipnis J, Schwartz M. (2002), Dual Action of Glatiramer Acetate (Cop-1) as a Treatment for Autoimmune Diseases and a Vaccine for Protective Autoimmunity after CNS Injury. Trends Mol. Med. 8:319-323.

Kipnis J, Mizrahi T, Hauben E, Shaked I, Shevach E, Schwartz M (2002a) Neuroprotective autoimmunity: naturally occurring CD4+CD25+ regulatory T cells suppress the ability to withstand injury to the central nervous system. Proc Natl Acad Sci USA 99:15620-15625

Kipnis J, Yoles E, Mizrahi T, Ben-Nun A, Schwartz M. (2002b) Myelin specific Th1 cells are necessary for post-traumatic protective autoimmunity. J. Neuroimmunol. 130:78-85.

Kipnis J, Nevo U, Panikashvili D, Alexandrovich A, Yoles E, Akselrod S, Shohami E, Schwartz M. (2003) Therapeutic vaccination for closed head injury. J. Neurotrauma 20(6): 559-569.

Kipnis J, Avidan H, Markovich Y, Mizrahi T, Hauben E, Prigozhina T B, Slavin S, Schwartz M. (2004a) Low-dose gamma-irradiation promotes survival of injured neurons in the central nervous system via homeostasis-driven proliferation of T cells. Eur. J. Neurosci. 19: 1191-1198.

Kipnis J, Avidan H, Schwartz M. (2004b) Dual effect of CD4+CD25+ regulatory T cells in neurodegeneration: Pro- and anti-inflammatory cytokines determine microglial activity. Proc Natl Acad Sci USA. 101 Suppl 2:14663-14669.

Kohm A P, Carpentier P A, Anger H A, Miller S D. (2002) Cutting edge: CD4+CD25+ regulatory T cells suppress antigen-specific autoreactive immune responses and central nervous system inflammation during active experimental autoimmune encephalomyelitis. J. Immunol. 169: 4712-4716.

Mangiarini L, Sathasivam K, Seller M, Cozens B, Harper A, Hetherington C, Lawton M, Trottier Y, Lehrach H, Davies S W, Bates G P. (1996) Exon 1 of the HD gene with an expanded CAG repeat is sufficient to cause progressive neurological phenotype in transgenic mice. Cell 87(3): 493-506.

Menalled L B, Chesselet M F. (2002) Mouse models of Huntington's disease, Trends Pharmacol Sci 23(1): 32-39.

Mizrahi T, Hauben E, Schwartz M (2002) The tissue-specific self-pathogen is the protective self-antigen: the case of uveitis. J Immunol 169:5971-5977.

Moalem G, Leibowitz-Amit R, Yoles E, Mor F, Cohen I R, Schwartz M (1999a) Autoimmune T cells protect neurons from secondary degeneration after central nervous system axotomy. Nat Med 5:49-55.

Moalem G, Monsonego A, Shani Y, Cohen I R, Schwartz M. (1999b) Differential T cell response in central and peripheral nerve injury: connection with immune privilege. Faseb J. 13: 1207-1217.

Moalem G, Gdalyahu A, Shani Y, Otten U, Lazarovici P, Cohen I R, Schwartz M. (2000) Production of neurotrophins by activated T cells: implications for neuroprotective autoimmunity. J. Autoimmun. 15: 331-345.

Mohajeri M H, Saini K, Schultz J G, Wollmer M A, Hock C, Nitsch R M. (2002) Passive immunization against beta-amyloid peptide protects central nervous system (CNS) neurons from increased vulnerability associated with an Alzheimer's disease-causing mutation. J. Biol. Chem. 277: 33012-33017.

Palczewski K, Buczylko J, Ohguro H, Annan R S, Carr S A, Crabb J W, Kaplan M W, Johnson R S, Walsh K A. (1994) Characterization of a truncated form of arrestin isolated from bovine rod outer segments. Protein Sci. 3: 314-324.

Pepperberg D R, Okajima T L, Ripps H, Chader G J, Wiggert B. (1991) Functional properties of interphotoreceptor retinoid-binding protein. Photochem. Photobiol. 54: 1057-1060.

Perlmutter D H, (2002) The cellular response to aggregated proteins associated with human disease. J. Clin. Invest. 110: 1219-1220.

Puig J, Arendt A, Tomson F L, Abdulaeva G, Miller R, Hargrave P A, McDowell J H. (1995) Synthetic phosphopeptide from rhodopsin sequence induces retinal arrestin binding to photoactivated unphosphorylated rhodopsin. FEBS Lett. 362:185-188.

Qin L, Liu Y, Cooper C, Liu B, Wilson B, Hong J S. (2002) Microglia enhance beta-amyloid peptide-induced toxicity in cortical and mesencephalic neurons by producing reactive oxygen species. J. Neurochem. 83: 973-983.

Rapalino O, Lazarov-Spiegler O, Agranov E, Velan G J, Yoles E, Fraidakis M, Solomon A, Gepstein R, Katz A, Belkin M, Hadani M, Schwartz M (1998) Implantation of stimulated homologous macrophages results in partial recovery of paraplegic rats. Nat Med 4:814-.821.

Sakaguchi S, Sakaguchi N, Shimizu J, Yamazaki S, Sakihama T, Itoh M, Kuniyasu Y, Nomura T, Toda M, Takahashi T. (2001) Immunologic tolerance maintained by $CD25^+$ $CD4^+$ regulatory T cells: their common role in controlling autoimmunity, tumor immunity, and transplantation tolerance. Immunol. Rev. 182: 18-32.

Scherzinger E, Lurz R, Turmaine M, Mangiarini L, Hollenbach B, Hasenbank R, Bates G P, Davies S W, Lehrach H, Wanker E E. (1997) Huntingtin-encoded polyglutamine expansions form amyloid-like protein aggregates in vitro and in vivo. Cell. 90, 549-558.

Schori H, Yoles E, Schwartz M (2001a) T-cell-based immunity counteracts the potential toxicity of glutamate in the central nervous system. J Neuroimmunol 119:199-204.

Schori H, Kipnis J, Yoles E, WoldeMussie E, Ruiz G, Wheeler L A, Schwartz M. (2001b) Vaccination for protection of retinal ganglion cells against death from glutamate cytotoxicity and ocular hypertension: implications for glaucoma. Proc Natl Acad Sci USA 98:3398-3403.

Schori H, Yoles E, Wheeler L A, Raveh T, Kimchi A, Schwartz M. (2002) Immune-related mechanisms participating in resistance and susceptibility to glutamate toxicity. Eur J Neurosci 16: 557-64.

Schwartz M. (2004) Glaucoma and Alzheimer. International Glaucoma Review. 5-3: 431-432.

Schwartz M, Cohen I R. (2000) Autoimmunity can benefit self-maintenance. Immunol. Today 21: 265-268.

Schwartz M, Kipnis J. (2002a) Autoimmunity on alert: naturally occurring regulatory CD4(+)CD25(+) T cells as part of the evolutionary compromise between a 'need' and a 'risk'. Trends Immunol. 23:530-534.

Schwartz M, Kipnis J (2002b) Multiple sclerosis as a by-product of the failure to sustain protective autoimmunity: a paradigm shift. Neuroscientist 8: 405-413.

Schwartz M, Kipnis J (2003) Harm or heal—divergent effects of autoimmune neuroinflammation? Response from Schwartz and Kipnis. Trends Immunol 24:7-8.

Schwartz M, Moalem G, Leibowitz-Amit R, Cohen I R (1999) Innate and adaptive immune responses can be beneficial for CNS repair. Trends Neurosci. 22:295-299.

Schwartz M, Shaked I, Fisher J, Mizrahi T, Schori H (2003) Protective autoimmunity against the enemy within: fighting glutamate toxicity. Trends Neurosci 26:297-302.

Seddon B. (2000) The physiological role of regulatory T cells in the prevention of autoimmunity: generation, specificity and mode of action. Arch. Immunol. Ther. Exp. 48: 339-345.

Selkoe D J (1997) Cellular and molecular biology of the beta-amyloid precursor protein and Alzheimer's disease. In: The molecular and genetic basis of neurological disease. R. N. Rosenberg, S. B. Prusiner, S. DiMauro, and R. L. Barchi, editors. Butterworth-Heinemann. Boston, Mass., USA, pp. 601-611.

Selkoe D J (2002) Deciphering the genesis and fate of amyloid beta-protein yields novel therapies for Alzheimer disease. J Clin Invest 110(10):1375-1381.

Serpell L C, Berriman J, Jakes R, Goedert M, Crowther R A (2000). Fiber diffraction of synthetic α-synuclein filaments shows amyloid-like cross-β conformation. Proc. Natl. Acad. Sci. USA. 9: 4897-4902.

Shaked I, Porat Z, Gersner R, Kipnis J, Schwartz M (2004a) Early activation of microglia as antigen-presenting cells correlates with T cell-mediated protection and repair of the injured central nervous system. J Neuroimmunol 146:84-93.

Shaked I, Tochros D, Gersner R, Meiri S, Mordechai S, Xiao X, Hart R P, Schwartz M (2004b) Protective autoimmunity: Interferon gamma enables microglia to remove glutamate without evoking inflammatory mediators. J Neurochem In press.

Vieira P L, Heystek H C, Wormmeester J, Wierenga E A, Kapsenberg M L. (2003) Glatiramer acetate (copolymer-1, copaxone) promotes Th2 cell development and increased IL-10 production through modulation of dendritic cells. J Immunol. 170(9):4483-4488.

White A R, Enever P, Tayebi M, Mushens R, Linehan J, Brandner S, Anstee D, Collinge J, Hawke S (2003) Monoclonal antibodies inhibit prion replication and delay the development of prion disease. Nature 422: 80-83.

Yoles E, Hauben E, Palgi O, Agranov E, Gothilf A, Cohen A, Kuchroo V, Cohen I R, Weiner H, Schwartz M. (2001) Protective autoimmunity is a physiological response to CNS trauma. J. Neurosci. 21: 3740-3748.

Ziemssen T, Kumpfel T, Klinkert W E, Neuhaus O, Hohlfeld R. (2002) Glatiramer acetate-specific T-helper 1- and 2-type cell lines produce BDNF: implications for multiple sclerosis therapy. Brain-derived neurotrophic factor. Brain 125: 2381-2391.

The invention claimed is:

1. A method for treating a neurodegenerative disorder or disease selected from the group consisting of Huntington's disease and Alzheimer's disease, said method comprising administering to an individual in need thereof an active agent selected from the group consisting of (i) Copolymer 1, (ii) a Copolymer 1-related peptide, (iii) a Copolymer 1-related polypeptide, and (iv) T cells activated with (i), (ii) or (iii).

2. The method in accordance with claim 1, wherein said active agent is Copolymer 1.

3. The method in accordance with claim 1, wherein said active agent is T cells which have been activated by Copolymer 1.

4. A method for reducing disease progression, and/or for protection from neurodegeneration in a patient suffering from Alzheimer's disease, which comprises administering to an individual in need thereof an effective amount of an active agent selected from the group consisting of (i) Copolymer 1, (ii) a Copolymer 1-related peptide, (iii) a Copolymer 1-related polypeptide, and (iv) T cells activated with (i), (ii) or (iii).

5. A method for reducing disease progression, and/or for protection from neurodegeneration in a patient suffering from Huntington's disease, which comprises administering to said patient in need thereof an effective amount of an active agent selected from the group consisting of (i) Copolymer 1, (ii) a Copolymer 1-related peptide, (iii) a Copolymer 1-related polypeptide, and (iv) T cells activated with (i), (ii) or (iii).

6. A method for treatment of a patient suffering from a neurodegenerative disease or disorder selected from the group consisting of Huntington's disease and Alzheimer's disease, which comprises immunizing said patient with a vaccine comprising an amount of Copolymer 1 effective for reducing disease progression in said patient.

7. A method for treatment of a patient suffering from neurodegenerative disease or disorder selected from the group consisting of Huntington's disease and Alzheimer's disease, which comprises immunizing said patient with a vaccine comprising an amount of Copolymer 1 effective for protection from neurodegeneration in said patient.

8. A method for treating neurodegeneration associated with Huntington's disease or Alzheimer's disease, said method comprising administering to an individual in need an active agent selected from the group consisting of (i) Copolymer 1, (ii) a Copolymer 1-related peptide, (iii) a Copolymer 1-related polypeptide, and (iv) T cells activated with (i), (ii) or (iii).

9. The method according to claim 8, wherein said active agent is Copolymer 1.

10. The method in accordance with claim 2, wherein said neurodegenerative disorder or disease is Alzheimer's disease.

11. The method in accordance with claim 2, wherein said neurodegenerative disorder or disease is Huntington's disease.

12. The method in accordance with claim 6, wherein said neurodegenerative disease or disorder is Alzheimer's disease.

13. The method in accordance with claim 6, wherein said neurodegenerative disease or disorder is Huntington's disease.

14. The method in accordance with claim 7, wherein said neurodegenerative disease or disorder is Alzheimer's disease.

15. The method in accordance with claim 7, wherein said neurodegenerative disease or disorder is Huntington's disease.

16. The method in accordance with claim 9, wherein said neurodegeneration is associated with Alzheimer's disease.

17. The method in accordance with claim 9, wherein said neurodegeneration is associated with Huntington's disease.

\* \* \* \* \*

SEQUENCE LISTING

```
<160> NUMBER OF SEQ ID NOS: 32

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Ala Ala Ala Tyr Ala Ala Ala Ala Ala Lys Ala Ala Ala Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Ala Glu Lys Tyr Ala Ala Ala Ala Ala Lys Ala Ala Ala Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide

<400> SEQUENCE: 3

Ala Lys Glu Tyr Ala Ala Ala Ala Ala Lys Ala Ala Ala Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Ala Lys Lys Tyr Ala Ala Ala Ala Ala Lys Ala Ala Ala Ala
1               5                   10                  15

<210> SEQ ID NO 5
```

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

Ala Glu Ala Tyr Ala Ala Ala Ala Ala Lys Ala Ala Ala Ala Ala
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Lys Glu Ala Tyr Ala Ala Ala Ala Ala Lys Ala Ala Ala Ala Ala
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Ala Glu Glu Tyr Ala Ala Ala Ala Ala Lys Ala Ala Ala Ala Ala
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Ala Ala Glu Tyr Ala Ala Ala Ala Ala Lys Ala Ala Ala Ala Ala
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Glu Lys Ala Tyr Ala Ala Ala Ala Ala Lys Ala Ala Ala Ala Ala
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Ala Ala Lys Tyr Glu Ala Ala Ala Ala Lys Ala Ala Ala Ala Ala
 1               5                  10                  15

<210> SEQ ID NO 11
<211> LENGTH: 15
```

```
<212> TYPE: PRT
<213> ORGANISM: Artificial Sequence
<220> FEATURE:
<223> OTHER INFORMATION: Synthetic peptide

<400> SEQUENCE: 11

Ala Ala Lys Tyr Ala Glu Ala Ala Ala Lys Ala Ala Ala Ala Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Glu Ala Ala Tyr Ala Ala Ala Ala Ala Lys Ala Ala Ala Ala Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Glu Lys Lys Tyr Ala Ala Ala Ala Ala Lys Ala Ala Ala Ala Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide

<400> SEQUENCE: 14

Glu Ala Lys Tyr Ala Ala Ala Ala Ala Lys Ala Ala Ala Ala Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

Ala Glu Lys Tyr Ala Ala Ala Ala Ala Ala Ala Ala Ala Ala Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Ala Lys Glu Tyr Ala Ala Ala Ala Ala Ala Ala Ala Ala Ala Ala
1               5                   10                  15

<210> SEQ ID NO 17
<211> LENGTH: 15
<212> TYPE: PRT
```

<213> ORGANISM: Artificial Sequence
<220> FEATURE:
<223> OTHER INFORMATION: Synthetic peptide

<400> SEQUENCE: 17

Ala Lys Lys Tyr Glu Ala Ala Ala Ala Ala Ala Ala Ala Ala Ala
1               5                   10                  15

<210> SEQ ID NO 18
<211> LENGTH: 15
<212> TYPE: PRT
<213> ORGANISM: Artificial Sequenece
<220> FEATURE:
<223> OTHER INFORMATION: Synthetic peptide

<400> SEQUENCE: 18

Ala Lys Lys Tyr Ala Glu Ala Ala Ala Ala Ala Ala Ala Ala Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Ala Glu Ala Tyr Lys Ala Ala Ala Ala Ala Ala Ala Ala Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

Lys Glu Ala Tyr Ala Ala Ala Ala Ala Ala Ala Ala Ala Ala Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Ala Glu Glu Tyr Lys Ala Ala Ala Ala Ala Ala Ala Ala Ala Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

Ala Ala Glu Tyr Lys Ala Ala Ala Ala Ala Ala Ala Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Glu Lys Ala Tyr Ala Ala Ala Ala Ala Ala Ala Ala Ala Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Ala Ala Lys Tyr Glu Ala Ala Ala Ala Ala Ala Ala Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Ala Ala Lys Tyr Ala Glu Ala Ala Ala Ala Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

Glu Lys Lys Tyr Ala Ala Ala Ala Ala Ala Ala Ala Ala Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

Glu Ala Lys Tyr Ala Ala Ala Ala Ala Ala Ala Ala Ala Ala Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

Ala Glu Tyr Ala Lys Ala Ala Ala Ala Ala Ala Ala Ala Ala Ala
1               5                   10                  15

<210> SEQ ID NO 29
<211> LENGTH: 15
<212> TYPE: PRT
<213> ORGANISM: Artificial Sequence
<220> FEATURE:

```
<223> OTHER INFORMATION: Synthetic peptide

<400> SEQUENCE: 29

Ala Glu Lys Ala Tyr Ala Ala Ala Ala Ala Ala Ala Ala Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

Glu Lys Tyr Ala Ala Ala Ala Ala Ala Ala Ala Ala Ala Ala Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic peptide

<400> SEQUENCE: 31

Ala Tyr Lys Ala Glu Ala Ala Ala Ala Ala Ala Ala Ala Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide

<400> SEQUENCE: 32

Ala Lys Tyr Ala Glu Ala Ala Ala Ala Ala Ala Ala Ala Ala Ala
1               5                   10                  15
```